US010288624B2

(12) United States Patent
Pang et al.

(10) Patent No.: US 10,288,624 B2
(45) Date of Patent: May 14, 2019

(54) METHOD OF PREDICTING ANIMAL LITTER SIZE USING PROTEIN BIOMARKERS RELATED WITH FERTILITY, AND METHOD OF PREDICTING ANIMAL SPERM QUALITY AND LITTER SIZE USING CHLORTETRACYCLINE STAINING

(71) Applicant: CHUNG ANG UNIVERSITY INDUSTRY ACADEMIC COOPERATION FOUNDATION, Seoul (KR)

(72) Inventors: Myung-Geol Pang, Seoul (KR); Woo-Sung Kwon, Seoul (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 176 days.

(21) Appl. No.: 14/711,741

(22) Filed: May 13, 2015

(65) Prior Publication Data

US 2016/0154002 A1    Jun. 2, 2016

(30) Foreign Application Priority Data

Dec. 1, 2014    (KR) .................. 10-2014-0169854

(51) Int. Cl.
*G01N 33/68*     (2006.01)
*G01N 33/569*    (2006.01)

(52) U.S. Cl.
CPC ..... *G01N 33/689* (2013.01); *G01N 33/56966* (2013.01)

(58) Field of Classification Search
None
See application file for complete search history.

(56) References Cited

U.S. PATENT DOCUMENTS

| 4,816,567 | A | 3/1989 | Cabilly et al. | |
|---|---|---|---|---|
| 2008/0138797 | A1* | 6/2008 | Hunt | B82Y 5/00 435/6.16 |
| 2009/0253160 | A1* | 10/2009 | Pang | A01K 67/02 435/29 |
| 2015/0045610 | A1 | 2/2015 | Mosinger | |

FOREIGN PATENT DOCUMENTS

| JP | 2001509006 A | 7/2001 |
|---|---|---|
| JP | 2008249587 A | 10/2008 |
| JP | 2011501659 A | 1/2011 |
| WO | 9803682 A1 | 1/1998 |
| WO | 2009045289 A2 | 4/2009 |
| WO | WO2014035840 A1 | 3/2014 |

OTHER PUBLICATIONS

Soggiu et al., Mol. BioSyst., published Jan. 21, 2013; 9: 1188-1195.*
Reyes et al., International Journal of Andrology, 1987; 10: 507-515.*
Gao et al., Arch Toxicol., 2012; 86: 1443 https://doi.org/10.1007/s00204-012-0825-3—Author Manuscript; 16 pages total. (Year: 2012).*
Maňásková, Journal of Reproductive Immunology, 2008; 78: 40-48. (Year: 2008).*
Kwon et al., Molecular & Cellular Proteomics 14: 10.1074/mcp M114.045369, 1230-1240, Epub: Feb. 18, 2015. (Year: 2015).*
Song et al., Theriogenology, 2010; 73: 551-559. (Year: 2010).*
Shannon, P., et al., "Toxic Effect and Action of Dead Sperm on Diluted Bovine Semen", Journal of Dairy Science, May 1972, pp. 614-620, vol. 55, No. 5.
Upreti, G., et al., "Studies on aromatic amino acid oxidase activity in ram spermatozoa: role of pyruvate as an antioxidant", Animal Reproduction Science, May 29, 1998, pp. 275-287, vol. 51.
Conner, S., et al., "Chapter 3: Genomic and proteomic approaches to defining sperm production and function", "The Sperm Cell: Production, Maturation, Fertilization, Regeneration", 2006, pp. 49-71, Publisher: Cambridge University Press, Published in: New York.
Arcelay, E., et al., "Identification of proteins undergoing tyrosine phosphorylation during mouse sperm capacitation", "Int. J. Dev. Biol.", Jun. 24, 2008, pp. 463-472, vol. 52.
Bendahmane, M., et al., "Calmodulin Signals Capacitation and Triggers the Agonist-Induced Acrosome Reaction in Mouse Spermatozoa", "Archives of Biochemistry and Biophysics", Jun. 1, 2001, pp. 1-8, vol. 390, No. 1.

(Continued)

*Primary Examiner* — Christina M Borgeest
(74) *Attorney, Agent, or Firm* — Hultquist, PLLC; Steven J. Hultquist

(57) ABSTRACT

The present invention relates to a method of predicting animal litter size using a fertility-related protein marker, and more particularly, to the discovery of a sperm marker that is expressed differently depending on animal fertility, a marker composition for predicting litter size, which comprises an antibody that binds specifically to the marker, and a method of predicting animal litter size using the marker composition. Moreover, the present invention relates to a method of predicting animal semen quality and litter size by chlortetracycline staining, and more particularly, to a method of predicting of animal litter size by measuring the motility, motion kinematics or capacitation status of sperm. When the animal sperm-derived protein marker according to the present invention is used, the litter size of individuals can be predicted by analyzing a protein that is expressed differently depending on litter size. When the method of animal semen quality and litter size by chlortetracycline staining is used, the fertility of sperm and the litter size of individuals can be predicted. According to the present invention, superior species having high sperm fertility and high litter size can be selected based on information provided by the method. Thus, the present invention is highly useful for the sustainable production of animals.

5 Claims, 6 Drawing Sheets

(56) References Cited

OTHER PUBLICATIONS

Bonde, J., et al., "Relation between semen quality and fertility: a population-based study of 430 first-pregnancy planners", "The Lancet", Oct. 10, 1998, pp. 1172-1177, vol. 352.

Braundmeier, A., et al., "Invited Review: The Search is on: Finding Accurate Molecular Markers of Male Fertility", "Journal of Dairy Science", 2001, pp. 1915-1925, vol. 84, No. 9.

Budworth, P., et al., "Relationships Between Computerized Measurements of Motion of Frozen-Thawed Bull Spermatozoa and Fertility", "Journal of Andrology", Jan./Feb. 1988, pp. 41-54, vol. 9, No. 1.

Calvete, J., et al., "Characterization of two glycosylated boar spermadhesins", "Eur. J. Biochem.", 1993, pp. 719-725, vol. 218.

Clackson, T., et al., "Making antibody fragments using phage display libraries", "Nature", Aug. 15, 1991, pp. 624-628, vol. 352.

Colas, C., et al., "Changes in calmodulin immunocytochemical localization associated with capacitation and acrosomal exocytosis of ram spermatozoa", "Theriogenology", Mar. 15, 2009, pp. 789-800, vol. 71, No. 5.

Conner, S., et al., "Genomic and proteomic approaches to defining sperm production and function", "The Sperm Cell: Production, Maturation, Fertilization, Regeneration", Aug. 2009, pp. 49-71 (Abstract), Publisher: Cambridge University Press.

Cordoba, M., et al., "Differential activities of malate and isocitrate NAD(P)-dependent dehydrogenases are involved in the induction of capacitation and acrosome reaction in cryopreserved bovine spermatozoa", "Andrologia", Feb. 2005, pp. 40-45, vol. 37.

Dostalova, Z., et al., "Quantitation of boar spermadhesins in accessory sex gland fluids and on the surface of epididymal, ejaculated and capacitated spermatozoa", "Biochimica et Biophyisca Acta", May 25, 1994, pp. 48-54, vol. 1200.

Fearnley, I., et al., "NADH: ubiquinone oxidoreductase from bovine heart mitochondria: cDNA sequences of the import precursors of the nuclear-encoded 39 kDa and 42 kDa subunits", "Biochem. J.", Sep. 15, 1991, pp. 821-829, vol. 278.

Fraser, L., et al., "A glycolytic product is obligatory for initiation of the sperm acrosome reaction and whiplash motility required for fertilization in the mouse", "J. Reprod. Fert.", Jan. 1981, pp. 25-35, vol. 61.

Fraser, L., et al., "Ca2+-related changes in the mouse sperm capacitation state: a possible role for Ca2+-ATPase", "J. Reprod. Fert.", Sep. 1992, pp. 363-377, vol. 96.

Gadea, J., "Sperm factors related to in vitro and in vivo porcine fertility", "Theriogenology", Jan. 15, 2005, pp. 431-444, vol. 63.

Gerrits, R., et al., "Perspectives for artificial insemination and genomics to improve global swine populations", "Theriogenology", Jan. 15, 2005, pp. 283-299, vol. 63.

Hao, J., et al., "Equatorin is not essential for acrosome biogenesis but is required for the acrosome reaction", "Biochemical and Biophysical Research Communications", Jan. 27, 2014, pp. 537-542, vol. 444.

Kirichok, Y., et al., "Whole-cell patch-clamp measurements of spermatozoa reveal an alkaline-activated Ca2+ channel", "Nature", Feb. 9, 2006, pp. 737-740, vol. 439.

Kohsaka, T., et al., "A new technique for the precise location of lactate and malate dehydrogenases in goat, boar and water buffalo spermatozoa using gel incubation film", "J. Reprod. Fert.", 1992, pp. 201-209, vol. 95.

Kwon, W., et al., "Voltage-dependent anion channels are a key factor of male fertility", "Fertility and Serililty", Feb. 2013, pp. 354-361, vol. 99, No. 2.

Kwon, W., et al., "A proteomic study to predict litter size in boar spermatozoa", "Dev. Reprod.", Sep. 2014, pp. 28-31, Supplement 1, vol. 18.

Kwon, W., et al., "Vasopressin Effectively Suppresses Male Fertility", "Plos One", Jan. 24, 2013, pp. 1-8, e54192, vol. 8, No. 1.

Kwon, W., et al., "Comprehensive Proteomic Study to Predict Male Fertility in Spermatozoa", "The 14th International Symposium on Developmental Biotechnology: Bioethics in animal reproduction research", Oct. 24, 2014, p. 97, Publisher: Korean Society of Embryo Transfer, Published in: Seoul, Republic of Korea.

Lasko, J., et al., "Calcium/calmodulin and cAMP/protein kinase-A pathways regulate sperm motility in the stallion", "Animal Reproduction Science", May 24, 2012, pp. 169-177, vol. 132.

Lewis, S., "Focus on Determinants of Male Fertility: Is sperm evaluation useful in predicting human fertility?", "Reproduction", 2007, pp. 31-40, vol. 134.

Loza-Huerta, A., et al., "Certain Strongylocentrotus purpuratus sperm mitochondrial proteins co-purify with low density detergent-insoluble membranes and are PKA or PKC-substrates possibly involved in sperm motility regulation", "Biochimica et Biophysica Acta", Aug. 6, 2013, pp. 5305-5315, vol. 1830.

Manandhar, G., et al., "Exposure of Sperm Head Equatorin after Acrosome Reaction and Its Fate after Fertilization in Mice", "Biology of Reproduction", 2001, pp. 1425-1436, vol. 65.

Mateo, S., et al., "Marked correlations in protein expression identified by proteomic analysis of human spermatozoa", "Proteomics", 2007, pp. 4264-4277, vol. 7.

Mohamed, E., et al., "Xenoestrogenic compounds promote capacitation and an acrosome reaction in porcine sperm", "Theriogenology", 2011, pp. 1161-1169, vol. 75.

Narmadha, G., et al., "Characterization of a Novel Lysozyme-Like 4 Gene in the Rat", "PLoS One", Nov. 15, 2011, pp. 1-10, e27659, vol. 6, No. 11.

Oh, S., et al., "Capacitation status of stored boar spermatozoa is related to litter size of sows", "Animal Reproduction Science", Jun. 4, 2010, pp. 131-138, vol. 121.

Oh, S., et al., "The sperm penetration assay predicts the litter size in pigs", "International Journal of Andrology", 2010, pp. 604-612, vol. 33.

Park, Y., et al., "Sperm Penetration Assay as an Indicator of Bull Fertility", "Journal of Reproduction and Development", Apr. 21, 2012, pp. 461-466, vol. 58, No. 4.

Procaccio, V., et al., "Mapping to 1q23 of the human gene (NDUFS2) encoding the 49-kDa subunit of the mitochondrial respiratory Complex I and immunodetection of the mature protein in mitochondria", "Mammalian Genome", 1998, pp. 482-484, vol. 9.

Rahman, M., et al., "Sperm Proteomics: Road to Male Fertility and Contraception", "International Journal of Endocrinology", Dec. 1, 2013, pp. 1-11, Article ID 360986, vol. 2013.

Ruiz-Pesini, E., et al., "Correlation of sperm motility with mitochondrial enzymatic activities", "Clinical Chemistry", 1998, pp. 1616-1620, vol. 44, No. 8.

Sanz, L., et al., "The amino acid sequence of AQN-3, a carbohydrate-binding protein isolated from boar sperm: Location of disulphide bridges", "Federation of European Biochemical Sciences", Oct. 7, 1991, pp. 33-36, vol. 291, No. 1.

Sanz, L., et al., "The complete primary structure of the spermadhesin AWN, a zona pellucida-binding protein isolated from boar spermatozoa", "Federation of European Biochemical Societies", Apr. 1992, pp. 213-218, vol. 300, No. 3.

Shannon, P., et al., "Kinetics of the aromatic L-amino acid oxidase from dead bovine spermatozoa and the effect of catalase on fertility of diluted bovine semen stored at 5 degrees celsius and ambient temperatures", "J. Reprod. Fert.", 1982, pp. 463-467, vol. 64.

Sharlip, I., et al., "Best practice policies for male infertility", "Fertility and Sterility", May 2002, pp. 873-882, vol. 77, No. 5.

Siva, A., et al., "Proteomics-based study on asthenozoospermia: differential expression of proteasome alpha complex", "Molecular Human Reproduction", Mar. 18, 2010, pp. 452-462, vol. 16, No. 7.

Sun, R., et al., "Lyzl4, a novel mouse sperm-related protein, is involved in fertilization", "Acta Biochim Biophys Sin", Mar. 28, 2011, pp. 346-353, vol. 43, No. 5.

Toshimori, K., et al., "An MN9 Antigenic Molecule, Equatorin, Is Required for Successful Sperm-Oocyte Fusion in Mice", "Biology of Reproduction", 1998, pp. 22-29, vol. 59.

Vilagran, I., et al., "Acrosin-binding protein (ACRBP) and triosephosphate isomerase (TPI) are good markers to predict boar sperm freezing capacity", "Theriogenology", Sep. 15, 2013, pp. 443-450, vol. 80, No. 5.

(56) References Cited

OTHER PUBLICATIONS

Visconti, P., "Understanding the molecular basis of sperm capacitation through kinase design", "PNAS", Jan. 20, 2009, pp. 667-668, vol. 106, No. 3.

Wu, L., et al., "Fucose, Mannose, and Beta-N-Acetylglucosamine Glycopolymers Initiate the Mouse Sperm Acrosome Reaction through Convergent Signaling Pathways", "ACS Chem. Biol.", Nov. 19, 2013, pp. 468-475, vol. 9.

Yoshinaga, K., et al., "Inhibition of mouse fertilization in vivo by intra-oviductal injection of an anti-equatorin monoclonal antibody", "Reproduction", 2001, pp. 649-655, vol. 122.

Zaneveld, L., et al., "Human sperm capacitation and the acrosome reaction", "Human Reproduction", 1991, pp. 1265-1274, vol. 6, No. 9.

Dyck, MK, et al., "Biological Markers of Boar Fertility", "Reproduction in Domestic Animals", 2011, pp. 55-58, vol. 46 (Suppl 2).

Novak, S., et al., "Seminal Plasma Proteins as Potential Markers of Relative Fertility in Boars", "Journal of Andrology", Mar./Apr. 2010, pp. 188-200, vol. 31, No. 2.

Park, Y.-J., et al., "The Proteomic Revolution to Improve Tools for Evaluating Male Fertility in Animals", "Journal of Proteome Research", Sep. 2013, pp. 4738-4747, vol. 12.

Harayama et al., "Influence of Calmodulin Upon Heads Agglutination During Capacitation Process of Pig Sperm", Research Report in Year 2000, 2000.

Harayama et al., "Influence of Calmodulin Upon Heads Agglutination During Capacitation Process of Pig Sperm", Research Report in Year 2000, 2000, (Machine Translation).

Xu, X. et al., "In Vitro Maturation and Fertilization Techniques for Assessment of Semen Quality and Boar Fertility", Journal of Animal Science, 1998, pp. 3079-3089, vol. 76.

\* cited by examiner

METHOD OF PREDICTING ANIMAL LITTER SIZE USING PROTEIN BIOMARKERS RELATED WITH FERTILITY, AND METHOD OF PREDICTING ANIMAL SPERM QUALITY AND LITTER SIZE USING CHLORTETRACYCLINE STAINING

CROSS-REFERENCE TO RELATED APPLICATION

This application claims priority under the provisions of 35 USC 119 to Korean Patent Application No. 10-2014-0169854 filed Dec. 1, 2014. The disclosure of Korean Patent Application No. 10-2014-0169854 is hereby incorporated herein by reference, in its entirety, for all purposes.

TECHNICAL FIELD

The present invention relates to a method of predicting animal litter size using a fertility-related protein marker, and more particularly, to the discovery of a sperm marker that is expressed differently depending on animal fertility, a marker composition for predicting litter size, which comprises an antibody that binds specifically to the marker, and a method of predicting animal litter size using the marker composition. Moreover, the present invention relates to a method of predicting animal semen quality and litter size by chlortetracycline staining, and more particularly, to a method of predicting of animal litter size by measuring the motility, motion kinematics or capacitation status of sperm.

BACKGROUND ART

Prediction and diagnosis of male animal fertility is a major concern of those skilled in the art. In humans, about half of the fertility problems arise due to male factors. In addition, 50% of breeding system failures that are contributed by sires (e.g., breeding cattle, breeding horses, breeding pigs, etc.) lead to huge economic drawbacks in the animal industry (Sharlip I D et al., Fertility Steril, 77(5):873-882, 2002). Therefore, the development of new methods is needed to ensure more accurate prediction and diagnosis of male fertility.

Worldwide, artificial insemination (AI) has been extensively performed in animal industries. Recent data revealed that more than 90% of the sows in Europe and the USA have been bred using AI during last three decades (Gerrits R J et al., Theriogenology, 63(2):283-299, 2005). Moreover, AI has been implemented extensively in swine industries for genetic up-gradation (Gadea J, Theriogenology, 63(2):431-444, 2005).

However, the selection of high-quality semen still depends on conventional sperm analyses such as the analysis of sperm morphology, motility, and sperm penetration assays (Bonde J P, Lancet, 352(9135):1172-1177, 1998; Budworth P R et al., J Androl, 9(1):41-54, 1998; Oh S A et al., Anim Reprod Sci, 121(1-2):131-138, 2010). Although these tests are commonly used to evaluate the male factor of fertility/infertility, the clinical value is still debated (Lewis S E, Reproduction, 134(1):31-40, 2007; Braundmeier A G, Journal of Dairy Science, 84:1915-1925, 2001).

To overcome the disadvantages of conventional sperm analyses, a new method capable of measuring sperm function and fertility on humans and economically important animal species should be developed. In addition, it is important to note that the optimization of sperm production will be possible when the methods to choose superior sires with greater efficiency become available.

Several recent studies reported that the use of proteomics as an effective tool aids in understanding the molecular biology of sperm. In fact, increased knowledge of the sperm proteome enabled new molecular markers to be identified (Corner J S et al., In The Sperm Cell, pp 49-71, 2006; de Mateo S et al., Proteomics, 7(23):4264-4277, 2007). In this regard, the identification of superior sire-derived protein biomarkers using proteomics tools will open up new horizons in the fields related to the reproduction of animals.

The ejaculated sperm of mammals undergoes physiological changes such as a capacitation procedure while it exists in the female genital tract for a long period of time (Zaneveld L J et al., Human Reproduction, 6:1265-1274, 1991; Fraser L R et al., Journal of Reproduction and Fertility, 96:363-377, 1992; Kirichok Y et al., Nature, 439:737-740, 2006; Visconti P E, PNAS, 106:667-668, 2009, Kwon W S et al., Fertil Steril, 99:354-61, 2013; Kwon W S et al., PLoS One, 8:e54192, 2013). Because sperm can be fertilized with oocytes after it undergoes the capacitation procedure, the difference between before and after the capacitation procedure is very important in view of sperm fertility. However, to date, studies on the difference in protein expression patterns between before and after capacitation have been mainly conducted without considering litter size.

Accordingly, the present inventors have made extensive efforts to develop a novel method for predicting litter size, and as a result, have found that, when a method of predicting litter size based on the difference in the expression level of a protein marker between before and after sperm capacitation, and a method of predicting semen quality and litter size by chlortetracycline staining based on whether sperm was capacitated, are used, the ability of an individual to produce litter can be effectively predicted, thereby completing the present invention.

DISCLOSURE OF INVENTION

Technical Problem

It is an object of the present invention to provide a biomarker for predicting animal litter size, a marker composition for predicting litter size, and a method of predicting animal litter size using the marker.

Another object of the present invention is to provide methods of predicting animal semen quality and animal litter size based on whether sperm was capacitated.

Technical Solution

The present invention provides a marker for predicting animal litter size, which is selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2), and has increased expression in animal semen.

The present invention also provides a composition for predicting animal litter size, which comprises an antibody that binds specifically to at least one marker selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2), and a kit for predicting animal litter size, which comprises the composition.

The present invention also provides a method for detecting a marker for predicting animal litter size, the method comprising the steps of: (a) adding a test sample to a support coated with at least one antibody, selected from anti-L-amino-acid oxidase (anti-LAAO), anti-mitochondrial malate dehydrogenase 2, NAD (anti-MDH2), anti-cytosolic 5'-nucleotidase 1B (anti-NT5C1B), anti-lysozyme-like protein 4 (anti-LYZL4), anti-calmodulin (anti-CALM), anti-equatorin (anti-EQTN), anti-spermadhesin AWN, anti-triosephosphate isomerase (anti-TPI), anti-Ras-related protein Rab-2A (anti-RAB2A), anti-spermadhesin AQN-3 and anti-NADH dehydrogenase [ubiquinone] iron-sulfur protein 2 (anti-NDUFS2) antibodies, to induce an antigen-antibody reaction; (b) detecting an antigen-antibody reaction product, produced in step (a), using a label-conjugated secondary antibody and a chromogenic substrate solution; and (c) comparing the level of an L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 or NADH dehydrogenase [ubiquinone] iron-sulfur protein 2 (NDUFS2), detected in step (b), with that of a control to thereby provide information for predicting litter size.

The present invention also provides a composition for predicting animal litter size, the composition comprising either a gene that encodes at least one marker selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2), or a primer or probe that binds specifically to the mRNA of the gene. The present invention also provides a kit for predicting animal litter size, which comprises the composition for predicting animal litter size.

The present invention also provides a method for predicting animal litter size, the method comprising the steps of: (a) measuring in a test sample the mRNA or protein level of a marker for predicting animal litter size, which is selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2); and (b) analyzing an increase or decrease in the mRNA or protein expression level.

The present invention also provides a method for predicting animal semen quality, the method comprising the steps of: (a) preparing spermatozoa extracted from an animal; (b) measuring a change in the motility or capacitation of the spermatozoa prepared in step (a); and (c) comparing a value, measured for the motility or capacitation of the spermatozoa in step (b), with a measured value for control sperm to thereby evaluate the quality of the spermatozoa.

The present invention also provides a method for predicting animal litter size, the method comprising the steps of: (a) preparing spermatozoa extracted from an animal; (b) measuring a change in the capacitation or acrosome reaction of the spermatozoa prepared in step (a); and (c) classifying the pattern of the capacitation or acrosome reaction of the spermatozoa, obtained in step (b), as an AR-, B- or F-pattern, comparing the percentage of each of the patterns with the percentage of the pattern of control spermatozoa, and predicting that the animal has a litter size of 12 or more when the AR-pattern percentage of the spermatozoa after capacitation is 17.5% or more, or when the difference in the AR-pattern percentage between before and after capacitation is 18.97% or more, or when the difference in the B-pattern percentage between before and after capacitation is 0.68% or less.

Advantageous Effects

When the animal sperm-derived protein marker according to the present invention is used, the litter size of individuals can be predicted by analyzing a protein that is expressed differently depending on litter size. When the method of animal semen quality and litter size by chlortetracycline staining is used, the fertility of sperm and the litter size of individuals can be predicted. According to the present invention, superior species having high sperm fertility and high litter size can be selected based on information provided by the method. Thus, the present invention is highly useful for the sustainable production of animals.

BRIEF DESCRIPTION OF THE DRAWINGS

FIG. 1A shows the protein spots of an individual having high litter size, and FIG. 1B shows the protein spots of an individual having low litter size.

FIG. 2A shows 6 proteins that are significantly highly expressed in sperm having low litter size, and FIG. 2B shows 5 proteins that are significantly highly expressed in sperm having high litter size. The data represent mean±SEM, n=3.

FIG. 3A shows the ratios (%) of RAB2A, TPI, NDUFS2, CALM, and MDH2 proteins (optical density (OD×mm)/α-tubulin (OD×mm)) in high- and low-litter size sperms and FIG. 3B shows the results of probing the proteins of FIG. 3A with anti-RAB2A, anti-TPI, anti-NDUFS2, anti-CALM, and anti-MDH2 antibodies.

FIG. 4A shows average litter size by the percentage of RAB2A expression level; FIG. 4B shows average litter size by the percentage of TPI expression level; FIG. 4C shows average litter size by the percentage of NDUFS2 expression level; FIG. 4D shows average litter size by the percentage of CALM expression level; and FIG. 4E shows average litter size by the percentage of MDH2 expression level.

FIG. 6A shows average litter size as a function of the percentage of AR pattern after capacitation; FIG. 6B shows average litter size as a function of the difference in AR pattern between before and after capacitation; and FIG. 6C shows average litter size as a function of the difference in B pattern between before and after capacitation.

BEST MODE FOR CARRYING OUT THE INVENTION

Figure 1A:
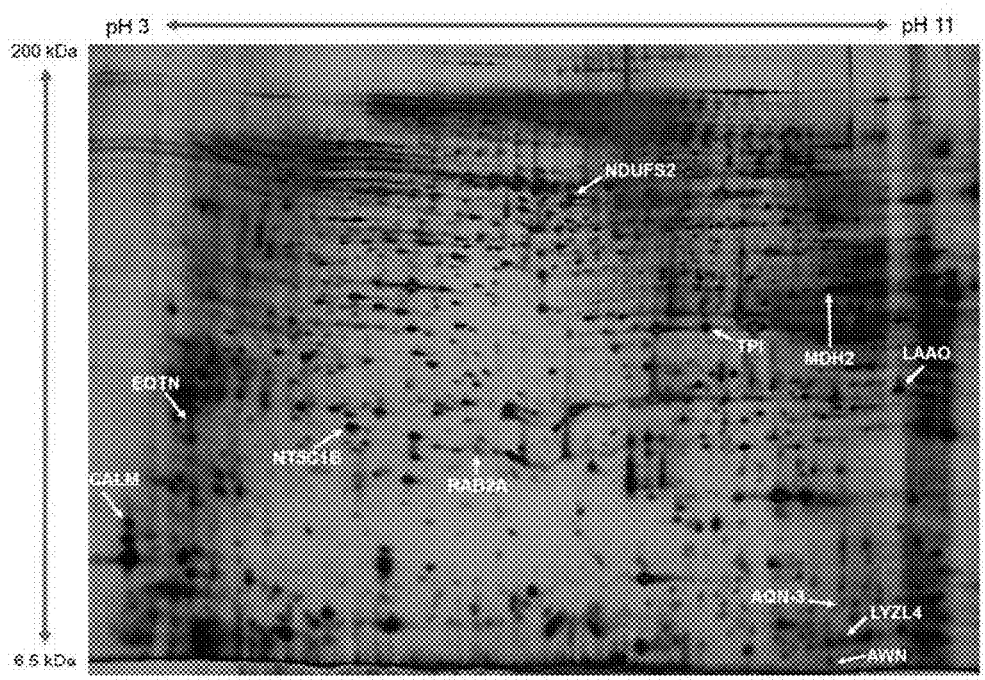
FIGS. 1A and 1B show the results obtained by separating animal sperm proteins by two-dimensional electrophoresis (2-DE), staining the 2-DE gels with silver nitrate and analyzing the stained gels using PDQuest SW. Specifically.
Figure 1B:
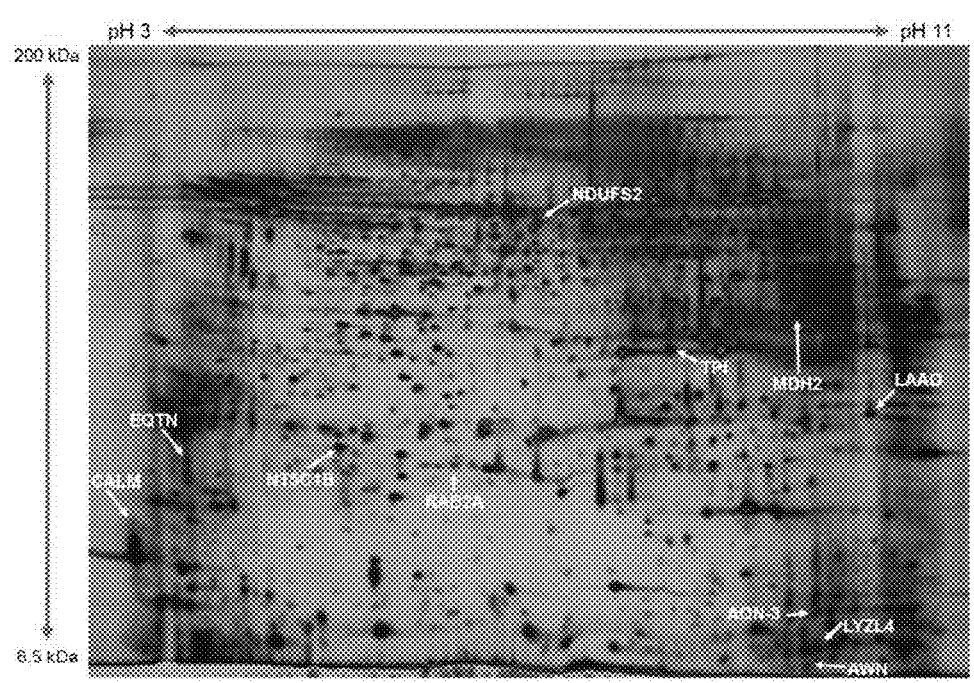
Figure 2A:
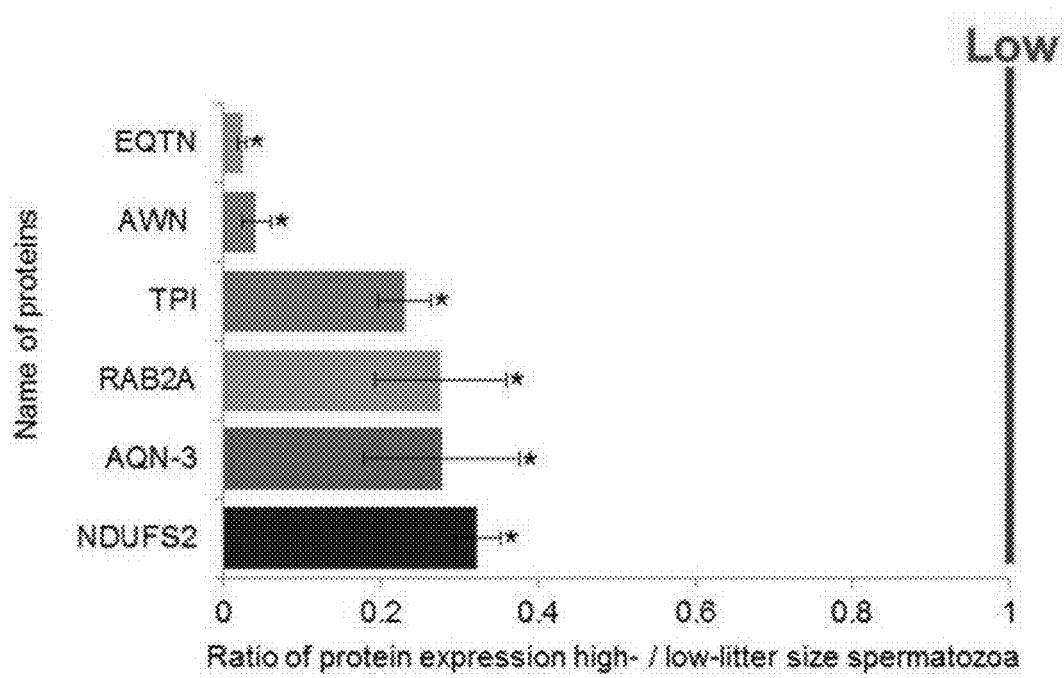
FIGS. 2A and 2B show proteins that are expressed differently (>3-fold) between an individual having high litter size and an individual having low litter size (P*<0.05). Specifically.

In an example of the present invention, boars were divided into a high-litter size group (high litter size) and a low-litter size group (low litter size), and then spermatozoa were collected from each of the groups, and subjected to two-dimensional electrophoresis. Then, protein expression patterns in the high litter size and the low litter size were analyzed using ESI-MS/MS and compared between the high litter size and the low litter size. As a result, it was shown that proteins were expressed differentially between the high litter size and the low litter size (FIGS. 1 and 2). As shown in Table 2 below, the proteins expressed differently between the high litter size and the low litter size were L-amino-acid oxidase (LAAO), mitochondrial malate dehydrogenase 2, NAD (MDH2), cytosolic 5'-nucleotidase 1B (NT5C1B), lysozyme-like protein 4 (LYZL4), CALM (calmodulin), EQTN (equatorin), spermadhesin AWN, TPI (triosephosphate isomerase), RAB2A (Ras-related protein Rab-2A), spermadhesin AQN-3 and NDUFS2 (NADH dehydrogenase [ubiquinone] iron-sulfur protein 2). Particularly, it could be seen that EQTN, AWN, TPI, RAB2A, AQN-3 or NDUFS2 was significantly highly expressed in the low-litter size spermatozoa compared to in the high-litter size spermatozoa (>3-fold; $P<0.05$; FIG. 2A), and LAAO, MDH2, NT5C1B, LYZL4 or CALM was significantly highly expressed in the high-bitter size spermatozoa as compared to the low-litter size spermatozoa (>3-fold; $P<0.05$; FIG. 2A).

Thus, in one aspect, the present invention provides a marker for predicting animal litter size, which is selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2), and has increased expression in animal semen.

In the present invention, the animal may be any one selected from the group consisting of bovine, equine, porcine, ovine, elk and bison.

NCBI gi No. for the above markers and the markers used in the present invention are as follows (see Table 2):

NCBI gi No. of mitochondrial malate dehydrogenase 2, NAD (MDH2): 164541

NCBI gi No. of calmodulin (CALM): 2654179

NCBI gi No. of triosephosphate isomerase (TPI): 80971510

NCBI gi No. of Ras-related protein Rab-2A (RAB2A): 31125379

NCBI gi No. of NADH dehydrogenase [ubiquinone] iron-sulfur protein 2 (NDUFS2): 54582230

NCBI gi No. of L-amino-acid oxidase (LAAO): 54583217

NCBI gi No. of cytosolic 5'-nucleotidase 1B (NT5C1B): 33528584

NCBI gi No. of lysozyme-like protein 4 (LYZL4): 31126871

NCBI gi No. of equatorin (EQTN): 31124567

NCBI gi No. of spermadhesin AWN: 248304

NCBI gi No. of spermadhesin AQN-3: 114083

It was reported that EQTN (38-48 KDa) protein is located and preserved in the equatorial segment and acrosomal region of animal species, and then exposed after acrosome reaction to facilitate sperm-oocyte interaction and fertilization processes (Toshimori K et al., Biol Reprod, 59(1):22-9, 1998; Yoshinaga K et al., Reproduction, 122(4):649-55, 2001; Hao J et al., BBRC, 444(4):537-542, 2014; Manandhar G et al., Biol Reprod, 65(5):1425-1436, 2011). Recent studies have reported that Eqtn knockout mouse (Eqtn−/−) spermatozoa have a deficiency in acrosome reaction and fertilization, but they have normal motility and morphology (Hao J et al., BBRC, 444(4):537-542, 2014).

It is known that RAB2A protein is a subgroup of the RAB family, which regulates vesicular transport and membrane fusion, and is located in the acrosome membrane of spermatozoa. Therefore, it has been reported that RAB2A is involved in the structural modification of the acrosome to induce acrosome reaction after spermatozoa capacitation (Rahman M S et al., Int J Endocrinol, 360986, 2013; Wu L et al., ACS Chem Bio, 9(2):468-475, 2014).

AQN-3 and AWN proteins have been identified in low-molecular mass in boar spermatozoa (Sanz L et al., FEBS Lett, 291(1):33-36, 1991; Sanz L et al., FEBS Lett, 300(3): 213-218, 1992). The proteins represent ZP-binding proteins, which have 109-133 amino acids and two disulfide bonds (Calvete J J et al., Eur J Biochem, 218(2):719-725, 1993). It is known that large amounts of these proteins coat the sperm surface after ejaculation, and are released after capacitation. It has been reported that AQN-3 and AWN play an important role in capacitation and gamete recognition (Dostalova et al., Biochim Biophys Acta, 1200(1):48-54, 1994).

NDUFS2 protein is known as a NADH-ubiquinone oxidoreductase 49 kDa subunit (Fearnley I M et al., Biochem J, 278(Pt 3):821-829, 1991; Procaccio V et al., Mamm Genome, 9(6):482-484, 1998), and NADH dehydrogenase contributes to site I of the mitochondrial electron transport chain. It has been reported that, in spermatozoa, NADH dehydrogenase is involved in tyrosine phosphorylation and sperm motility (Ruiz-Pesini E et al., Clin Chem, 44(8 Pt 1):1616-1620, 1998; Arcelay E et al., Int J Dev Biol, 52(5-6):463-472, 2008; Loza-Huerta et al., Biochim Biophys Acta, 1830(11):5305-5315, 2013).

TPI protein is an essential enzyme that is required for capacitation and acrosome reaction (Fraser L R et al., J Reprod Fertil, 61(1):25-35, 1981). However, it has been reported that, when TPI is highly expressed, it reduces sperm motility (asthenozoosperma) and sperm freezability (Siva A B et al., Mol Hum Reprod, 16(7):452-462, 2010; Vilagran I et al., Theriogenology, 80(5):443-450, 2013).

It is known that LAAO protein is located in the bovine sperm tail and is activated after sperm cell senescence and death (Shannon P et al., J Reprod Fertil, 64(2):469-473, 1982; Shannon P et al., J Reprod Fertil, 64(2):463-467, 1982).

It is known that MDH protein plays an important role in cellular respiration, is located in the mid-piece of mammalian spermatozoa (ram, boar, and buffalo), and contributes to capacitation and acrosome reaction (Kohsaka T et al., J Reprod Fertil, 95(1):201-209, 1992; Cordoba M et al., Andrologia, 37(1):40-46, 2005).

It has been reported that LYZL4 protein is located in the acrosome region of sperm, and plays a key role in fertilization processes that control motility and the acrosome reaction (Sun R et al., Acta Biochim Biophys Sin(Shanghai), 43(5):346-53, 2011; Narmadha G et al., PLoS ONE, 6(11): e27659, 2011).

It was reported that CALM protein is located in the acrosome region and flagellum of spermatozoa, and plays an important role in sperm motility and acrosome reaction (Bendahmane M et al., Arch Biochem Biophys, 390(1):1-8, 2001; Colas C et al., Theriogenology, 71(5):789-800, 2009; Lasko J et al., Anim Reprod Sci, 132(3-4):169-177, 2012).

As used herein, "marker for predicting litter size" means an organic biomolecule that is expressed differently depending on animal litter size. Examples of the organic biomolecule include, but are not limited to, polypeptides, proteins, nucleic acids (e.g., mRNA, DNA, etc.), lipids, glycolipids, glycoproteins, and saccharides (e.g., monosaccharides, disaccharides, oligosaccharides, etc.).

In another aspect, the present invention is directed to a composition for predicting animal litter size, which comprises an antibody that binds specifically to at least one marker selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2).

In the present invention, the animal may be any one selected from the group consisting of bovine, equine, porcine, ovine, elk and bison.

In the present invention, the antibody may be a monoclonal antibody or a polyclonal antibody.

As used herein, the term "antibody" means a protein molecule that is directed toward an antigenic site and binds specifically thereto. The antibody may be produced by conventional methods known in the art, for example, a fusion method (Kohler et al., European Journal of Immunology, 6:511-519, 1976), a recombinant DNA method (U.S. Pat. No. 4,816,567) or a phage antibody library method (Clackson et al., Nature, 352:624-628, 1991). The antibody that is used in the present invention may be a monoclonal or polyclonal antibody, an immunologically-active antibody fragment (e.g., a Fab' or (Fab')2 fragment), an antibody heavy chain, a humanized antibody, an antibody light chain, a genetically engineered single-chain Fv molecule, a chimeric antibody, or the like.

In the present invention, the marker for predicting litter size or the composition for predicting litter size may be applied to male contraceptives.

In still another aspect, the present invention is directed to a kit for predicting animal litter size, which comprises the composition.

In the present invention, the kit for predicting animal litter size may further comprise: a label-conjugated secondary antibody that develops a color by reaction with a substrate; a chromogenic substrate solution to be reacted with the label; a washing solution; and an enzymatic reaction stopping solution. The label may be selected from the group consisting of HRP (horseradish peroxidase), alkaline phosphatase, colloid gold, fluorescein and dye, and the chromogenic substrate may be selected from the group consisting of TMB (3,3',5,5'-tetramethyl bezidine), ABTS [2,2'-azinobis(3-ethylbenzothiazoline-6-sulfonic acid)] and OPD (o-phenylenediamine).

In yet another aspect, the present invention is directed to a method for detecting a marker for predicting animal litter size, the method comprising the steps of: (a) adding a test sample to a support coated with at least one antibody, selected from anti-L-amino-acid oxidase (anti-LAAO), anti-mitochondrial malate dehydrogenase 2, NAD (anti-MDH2), anti-cytosolic 5'-nucleotidase 1B (anti-NT5C1B), anti-lysozyme-like protein 4 (anti-LYZL4), anti-calmodulin (anti-CALM), anti-equatorin (anti-EQTN), anti-spermadhesin AWN, anti-triosephosphate isomerase (anti-TPI), anti-Ras-related protein Rab-2A (anti-RAB2A), anti-spermadhesin AQN-3 and anti-NADH dehydrogenase [ubiquinone] iron-sulfur protein 2 (anti-NDUFS2) antibodies, to induce an antigen-antibody reaction; (b) detecting an antigen-antibody reaction product, produced in step (a), using a label-conjugated secondary antibody and a chromogenic substrate solution; and (c) comparing the level of an L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 or NADH dehydrogenase [ubiquinone] iron-sulfur protein 2 (NDUFS2), detected in step (b), with that of a control to thereby provide information for predicting litter size.

In the present invention, the animal may be any one selected from the group consisting of bovine, equine, porcine, ovine, elk and bison.

In the present invention, the support may be selected from the group consisting of a nitrocellulose membrane, a PVDF membrane, a well plate made of polyvinyl or polystyrene resin, and slide glass. The antigen-antibody reaction may be detected using a method selected from the group consisting of enzyme-linked immunosorbent assay (ELISA), radioimmunoassay (RIA), sandwich assay, Western blotting, immunoprecipitation, immunohistochemical staining, fluorescence immunoassay, enzyme-substrate color development, and antigen antibody agglutination assay.

In the present invention, the label may be selected from the group consisting of HRP (horseradish peroxidase), alkaline phosphatase, colloid gold, fluorescein and dye, and the chromogenic substrate may be selected from the group consisting of TMB (3,3',5,5'-tetramethyl bezidine), ABTS [2,2'-azinobis(3-ethylbenzothiazoline-6-sulfonic acid)] and OPD (o-phenylenediamine).

In a further aspect, the present invention is directed to a composition for predicting animal litter size, the composition comprising either a gene that encodes at least one marker selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2), or a primer or probe that binds specifically to the mRNA of the gene.

In the present invention, the animal may be any one selected from the group consisting of bovine, equine, porcine, ovine, elk and bison.

In the present invention, the composition may be a probe that can be hybridized under the strict hybridization of the gene and the mRNA of the gene.

As used herein, the term "primer" refers to a nucleic acid sequence having a short free hydroxyl group and substantially means a short nucleic acid sequence capable of forming a base pair with a complementary template and functioning as a starting point for copying a template strand.

As used herein, the term "non-specific amplification" refers to the amplification of nucleic acid sequences other than the target sequence which results from primers hybridizing to sequences other than the target sequence and then serving as a substrate for primer extension.

As used herein, the term "probe" refers to a nucleic acid fragment such as RNA or DNA, which consists of several to several hundred nucleotides and can bind specifically bind to mRNA, and may be labeled to identify the existence of a specific mRNA. The probe may be prepared as an oligonucleotide probe, a single-stranded DNA probe, a double-stranded DNA probe, or an RNA probe, or the like.

In a still further aspect, the present invention is directed to a kit for predicting animal litter size, which comprises the composition for predicting animal litter size.

In the present invention, the kit may be a PCR kit, an RT-PCR kit or a DNA chip.

In a yet further aspect, the present invention is directed to a method for predicting animal litter size, the method comprising the steps of: (a) measuring in a test sample the mRNA or protein level of a marker for predicting animal litter size, which is selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4), calmodulin (CALM), equatorin (EQTN), spermadhesin AWN, triosephosphate isomerase (TPI), Ras-related protein Rab-2A (RAB2A), spermadhesin AQN-3 and NADH dehydrogenase [ubiquinone] iron-sulfur protein 2 (NDUFS2); and (b) analyzing an increase or decrease in the mRNA or protein expression level.

In the present invention, the animal may be any one selected from the group consisting of bovine, equine, porcine, ovine, elk and bison.

In the present invention, step (a) of measuring the protein level may be performed using at least one antibody selected from anti-L-amino-acid oxidase (anti-LAAO), anti-mitochondrial malate dehydrogenase 2, NAD (anti-MDH2), anti-cytosolic 5'-nucleotidase 1B (anti-NT5C1B), anti-lysozyme-like protein 4 (anti-LYZL4), anti-calmodulin (anti-CALM), anti-equatorin (anti-EQTN), anti-spermadhesin AWN, anti-triosephosphate isomerase (anti-TPI), anti-Ras-related protein Rab-2A (anti-RAB2A), anti-spermadhesin AQN-3 and anti-NADH dehydrogenase [ubiquinone] iron-sulfur protein 2 (anti-NDUFS2) antibodies.

The method of the present invention may further comprise a step of predicting that the animal litter size is high if the mRNA or protein expression level of at least one, selected from the group consisting of L-amino-acid oxidase (LAAO), mitochondrial malate dehydrogenase 2, NAD (MDH2), cytosolic 5'-nucleotidase 1B (NT5C1B), lysozyme-like protein 4 (LYZL4) and CALM (calmodulin), in the sample, increases.

In the present invention, the animal litter size may be predicted to be high if the protein expression level of L-amino-acid oxidase (LAAO), mitochondrial malate dehydrogenase 2, NAD (MDH2), cytosolic 5'-nucleotidase 1B (NT5C1B), lysozyme-like protein 4 (LYZL4) or CALM (calmodulin) increases when the anti-L-amino-acid oxidase (anti-LAAO), anti-mitochondrial malate dehydrogenase 2, NAD (anti-MDH2), anti-cytosolic 5'-nucleotidase 1B (anti-NT5C1B), anti-lysozyme-like protein 4 (LYZL4) or anti-CALM (anti-calmodulin) antibody is used.

The method of the present invention may further comprise a step of predicting that the animal litter size is low if the mRNA or protein expression level of at least one, selected from the group consisting of EQTN (equatorin), spermadhesin AWN, TPI (triosephosphate isomerase), RAB2A (Ras-related protein Rab-2A), spermadhesin AQN-3 and NDUFS2 (NADH dehydrogenase [ubiquinone] iron-sulfur protein 2), in the sample, increases.

In the present invention, the animal litter size may be predicted to be low if the protein expression level of EQTN (equatorin), spermadhesin AWN, TPI (triosephosphate isomerase), RAB2A (Ras-related protein Rab-2A), spermadhesin AQN-3) or NDUFS2 (NADH dehydrogenase [ubiquinone] iron-sulfur protein 2) increases when the anti-EQTN (anti-equatorin), anti-spermadhesin AWN, anti-TPI (triosephosphate isomerase), anti-RAB2A (Ras-related protein Rab-2A), anti-spermadhesin AQN-3 or anti-NDUFS2 (anti-NADH dehydrogenase [ubiquinone] iron-sulfur protein 2) antibody is used.

In the present invention, an analysis method that is used to measure the mRNA expression level may be any method known in the art, and examples thereof include, but are not limited to, polymerase chain reaction (PCR), reverse transcription polymerase chain reaction (RT-PCR), competitive RT-PCR, real-time RT-PCR), RNase protection assay (RPA), Northern blotting, and DNA chip assay.

In the present invention, an analysis method that is used to measure the protein expression level may be an method known in the art, and examples thereof include, but are not limited to, Western blotting, enzyme linked immunosorbent assay (ELISA), radioimmunoassay (RIA), radioimmunodiffusion, Ouchterlony immunodiffusion, rocket immunoelectrophoresis, immunohistochemical staining, immunoprecipitation assay, complement fixation assay, fluorescence activated cell sorter (FACS), protein chip assay, etc.

In an example of the present invention, the correlations between litter size and sperm motility, motion kinematics and capacitation status were examined. As a result, as can be seen in Table 5 below, sperm motility and motion kinematics did not show a significant correlation with litter size before and after capacitation and in the capacitation status. In addition, the capacitation status before capacitation did not show a significant correlation with litter size. However, as can be seen in Table 6 below, acrosome reaction after capacitation showed a positive correlation with litter size ($r=0.375$; $P<0.05$). In addition, the difference ($\Delta$) in AR and B patterns between before and after capacitation showed a significant correlation. As can be seen in Table 6 below, the difference ($\Delta$) in AR pattern between before and after capacitation showed a positive correlation with litter size ($r=0.333$; $P<0.05$), and the difference ($\Delta$) in B pattern between before and after capacitation showed a negative correlation with litter size ($r=-196\ 0.477$; $P<0.05$).

Thus, in another further aspect, the present invention is directed to a method for predicting animal semen quality, the method comprising the steps of: (a) preparing spermatozoa extracted from an animal; (b) measuring a change in the motility or capacitation of the spermatozoa prepared in step (a); and (c) comparing a value, measured for the motility or capacitation of the spermatozoa in step (b), with a measured value for control sperm to thereby evaluate the quality of the spermatozoa.

In the present invention, the animal may be any one selected from the group consisting of bovine, equine, porcine, ovine, elk and bison, but is not limited thereto.

In the method of the present invention, the sperm in step (a) may be either non-capacitated sperm or sperm capacitated by heparin treatment.

In the present invention, the sperm motility may be measured using CASA (computer assisted sperm analysis).

In the present invention, the change in capacitation may be measured using CTC (chlortetracycline) and Hoechst 33258 staining.

In the present invention, the control sperm may be sperm collected from an animal having high litter size or low litter size.

In another still further aspect, the present invention is directed to a method for predicting animal litter size, the method comprising the steps of: (a) preparing spermatozoa extracted from an animal; (b) measuring a change in the capacitation or acrosome reaction of the spermatozoa prepared in step (a); and (c) classifying the pattern of the capacitation or acrosome reaction of the spermatozoa, obtained in step (b), as an AR-, B- or F-pattern, comparing the percentage of each of the patterns with the percentage of the pattern of control spermatozoa, and predicting that the animal has a litter size of 12 or more when the AR-pattern percentage of the spermatozoa after capacitation is 17.5% or more, or when the difference in the AR-pattern percentage between before and after capacitation is 18.97% or more, or when the difference in the B-pattern percentage between before and after capacitation is 0.68% or less.

In the present invention, the animal may be any one selected from the group consisting of bovine, equine, porcine, ovine, elk and bison, but is not limited thereto.

In the present invention, the sperm in step (a) may be either non-capacitated sperm or sperm capacitated by heparin treatment, and step (b) of measuring the change in capacitation may be performed using CTC (chlortetracycline) and Hoechst 33258 staining. In addition, the control sperm in step (c) may be sperm collected from an animal having high litter size or low litter size.

EXAMPLES

Hereinafter, the present invention will be described in further detail with reference to examples. It will be obvious to a person having ordinary skill in the art that these examples are illustrative purposes only and are not to be construed to limit or change the scope of the present invention.

I. Method of Predicting Animal Litter Size Using a Fertility-Related Protein Marker Example I-1: Sample Preparation Landrace semen samples were provided from Sunjin Co. (Danyang, Korea). Fertility field data of each male were received from the farm (total pups/total breeding). To eliminate fertility variation, parity 1 was removed, and only parity 2-8 (multiparous) fertility data was included. Nine high-litter size semen samples (12.3±0.07) and nine low-litter size semen samples (10.2±0.09) were collected. Both samples were randomly divided into three groups (n=3) for experimental replication. To rule out individual variation, each group was pooled. The pooled samples were washed at 500×g for 20 min with a discontinuous Percoll gradient (70% [v/v] and 35% [v/v]) (Sigma, USA) to remove seminal plasma and dead spermatozoa. 20 boar samples randomly selected based on fertility field data of ELISA were also washed according to the above method. All procedures were performed according to guidelines for the ethical treatment of animals, and were approved by the Institutional Animal Care and Use Committee of Chung-Ang University.

Example I-2: CASA (Computer-Assisted Sperm Analysis)

Sperm motility (%) and motion kinematics were analyzed by computer-assisted sperm analysis using a CASA system (SAIS Plus version 10.1, Medical Supply, Seoul, Korea). Specifically, 10 µL of the sperm of each group prepared in Example 1 was placed in a Makler chamber (Makler, Israel). The filled chamber was then placed on a 37° C. heated stage. Using a 10× objective in phase contrast mode, the image was relayed, digitized, and analyzed by SAIS. The movement of at least 250 sperm cells was recorded for each sample from random fields (>5). With respect to the motility setting parameters, objects with a curvilinear velocity (VCL) more than 10 µm/s were considered motile. Motility (%) and five motion kinematics parameters (i.e., curvilinear velocity (VCL), straight-line velocity (VSL), average path velocity (VAP), and mean amplitude of head lateral displacement (ALH)) were analyzed.

Example I-3: Hoechst 33258/Chlortetracycline Fluorescence Assessment of Capacitation Status To determine capacitation status, a dual staining method was performed (Kwon W S et al., Fertil Steril, 99:354-61, 2013; Kwon W S et al., PLoS One, 8:e54192, 2013, Mohamed el-SA et al., Theriogenology, 75(6):1161-1169, 2011). Briefly, 135 µL of treated spermatozoa were added to 15 µL of H33258 solution (10 µg H33258/ml DPBS (Dulbecco's Phosphate-Buffered Saline)) and incubated for 2 min at room temperature. Excess dye was removed by layering the mixture over 250 µL of 2% (w/v) polyvinylpyrrolidone in DPBS. After centrifuging at 500×g for 5 min, the supernatant was discarded, and the pellet was resuspended in 100 µL of DPBS and 100 µL of a chlortetracycline fluorescence solution (750 mM CTC in 5 µl buffer: 20 mM Tris, 130 mM NaCl, and 5 mM cysteine, pH 7.4). Samples were observed with a Nikon microphot-FXA microscope (Tokyo, Japan) under epifluorescence illumination using ultraviolet BP 340-380/LP 425 and BP 450-490/LP 515 excitation/emission filters for H33258 and CTC, respectively. The spermatozoa were classified as live non-capacitated (F pattern, bright green fluorescence distributed uniformly over the entire sperm head, with or without a stronger fluorescent line at the equatorial segment), live capacitated (B pattern, green fluorescence over the acrosomal region and a dark postacrosome), or live acrosome reacted (AR, sperm showing a mottled green fluorescence over the head, green fluorescence only in the postacrosomal region, or no fluorescence over the head) (Kwon W S et al., Fertil Steril, 99:354-61, 2013; Kwon W S et al., PLoS One, e54192, 2013, Mohamed el-S A et al., Theriogenology, 75(6):1161-1169, 2011). Two slides per sample were evaluated with at least 400 spermatozoa per slide.

To evaluate sperm motion characteristics and capacitation status parameters in high- and low-litter size spermatozoa according to the methods of Example 1-2 and Example 1-3, CASA and H33258/CTC staining were performed. As a result, motility, motion kinematics, and capacitation status parameters were as follows: (1) for low-litter size spermatozoa, motility (MOT)=88.94±1.30%, VCL=152.92±10.40 μm/s, VSL=76.64±7.61 μm/s, VAP=88.71±6.11 μm/s, ALH=6.93±0.40 μm, AR=1.12±0.41%, F=91.55±3.92%, and B=7.33±3.72%; (2) for high-litter size spermatozoa, MOT=91.43±2.55%, VCL=159.10±9.89 μm/s, VSL=74.80±5.80 μm/s, VAP=87.53±10.47 μm/s, ALH=7.11±0.43 μm, AR=2.10±1.13%, F=87.14±0.63%, and B=10.75±0.97% (Table 1). Thus, it could be seen that sperm motility and capacitation status had no concern with litter size.

Table 1 below show the motility, motion kinematics and capacitation status of high-litter size spermatozoa and low-litter size spermatozoa.

TABLE 1

| Sperm motility, motion kinematics, and capacitation status | High-litter size spermatozoa | Low-litter size spermatozoa |
| --- | --- | --- |
| MOT (%) | 91.43 ± 2.55 | 88.94 ± 1.30 |
| VCL (μm/s) | 159.10 ± 9.89 | 152.92 ± 10.40 |
| VSL (μm/s) | 74.80 ± 5.80 | 76.64 ± 7.61 |
| VAP (μm/s) | 87.53 ± 10.47 | 88.71 ± 6.11 |
| ALH (μm) | 7.11 ± 0.43 | 6.93 ± 0.40 |
| AR (%) | 2.10 ± 1.13 | 1.12 ± 0.41 |
| F (%) | 87.14 ± 0.63 | 91.55 ± 3.92 |
| B (%) | 10.75 ± 0.97 | 7.33 ± 3.72 |

Sperm motility, motion kinematics and capacitation status are presented as mean ± SEM, n = 3. MOT = motility (%); VCL = curvilinear velocity (μm/s); VSL = straight-line velocity (μm/s); VAP = average path velocity (μm/s); ALH = mean amplitude of head lateral displacement (μm); AR = Live acrosome reacted pattern (%); F = Live non-capacitated pattern (%); B = Live capacitated pattern (%).

Example I-4: 2-DE and Gel Image Analysis

Spermatozoa samples (50×106/mL) were incubated for protein extraction in rehydration buffer containing 7M urea (Sigma), 2M thiourea (Sigma), 4% (w/v) CHAPS, 0.05% (v/v) Triton X-100 (Sigma), 1% (w/v) octyl β-D-glucopyranoside, 24 μM phenylmethysulfonylfluoride (PMSF), 1% (w/v) DTT, 0.5% (v/v) IPG buffer and 0.002% (w/v) BPB (bromophenol blue) at 4° C. for 1 hour. Then, 250 μg of solubilized protein from the sperm cells in 450 μL of rehydration buffer were placed in a rehydration tray with 24-cm NL Immobiline DryStrips (pH 3-11; Amersham) for 12 h at 4° C.

First-dimension electrophoresis was performed using an IPGphor isoelectric focusing apparatus, and then the strips were focused at 100 V for 1 hr, 200 V for 1 hr, 500 V for 1 hr, 1,000 V for 1 hr, 5,000 V for 1.5 hr, 8,000 V for 1.5 hr, and 8,000-90,000 V for 1 hr. After isoelectrofocusing, the strips were equilibrated with equilibration buffer A containing 6 M urea, 75 mM Tris-HCl (pH 8.8), 30% (v/v) glycerol, 2% (w/v) SDS (sodium dodecyl sulfate), 0.002% (w/v) BPB (bromophenol blue) and 2% (w/v) DTT for 15 min at room temperature. Then, the strips were equilibrated a second time with equilibration buffer B (equilibration buffer A with 2.5% (w/v) iodoacetamide (Sigma), but without DTT) for 15 min at room temperature.

Second-dimension electrophoresis was conducted with 12.5% (w/v) SDS-PAGE gels with the strips at 100 V for 1 h and 500 V until the bromophenol blue front began to migrate off of the lower end of the gels. The gels were silver-stained for image analysis. Detected spots were matched and analyzed by comparing them with high- and low-litter size spermatozoa gels using PDQuest 8.0 software (Bio-Rad). The low-fertility spermatozoa gel was used as a control. Finally, the density of the spots was calculated and normalized as the ratio of high-/low-litter size per spermatozoa gel.

Example I-5: Protein Identification 4-1: The proteins were subjected to in-gel trypsin digestion. Excised gel spots were destained with 100 μL of destaining solution (30 mM potassium ferricyanide, 100 mM sodium thiosulfate) while shaking for 5 min. After removing the solution, the gel spots were incubated in 200 mM ammonium bicarbonate for 20 min. The gel pieces were dehydrated with 100 μL of acetonitrile and dried in a vacuum centrifuge. The above procedure was repeated three times. The dried gel pieces were rehydrated with 20 μL of 50 mM ammonium bicarbonate containing 0.2 μg of modified trypsin (Promega) for 45 min on ice. After removing the solution, 30 μl of 50 mM ammonium bicarbonate were added. The digestion was performed overnight at 37° C. The peptide solution was desalted using a C18 nano-column (homemade).

4-2: Custom-made chromatographic columns were used for desalting and concentrating the peptide mixture prior to mass spectrometric analysis. A column consisting of 100-300 mL of Poros reverse phase R2 material (20-30 μm bead size, Perspective Biosystems) was packed into a constricted GELoader tip (Eppendorf). A 10 mL syringe was used to force liquid through the column by applying gentle air pressure. 30 μL of the peptide mixture from the digestion supernatant were diluted in 30 μL of 5% formic acid, loaded onto the column, and washed with 30 μL of 5% formic acid. For tandem mass spectrometry (MS/MS) analyses, the peptides were eluted with a solution of 1.5 μL of 50% methanol, 49% water and 1% formic acid directly into a pre-coated borosilicate nano-electrospray needle (EconoTip™).

4-3: EIS-MS/MS Analysis

MS/MS analysis of the peptides generated by in-gel digestion was performed using nano-electrospray ionization (ESI) on a Q-TOF2 mass spectrometer (AB Sciex Instruments). The source temperature was room temperature. A potential of 1 kV was applied to pre-coated borosilicate nano-electrospray needles in the ion source, combined with a nitrogen back-pressure of 0-5 psi to produce a stable flow rate (10-30 mL/min). The cone voltage was 40 V. The quadrupole analyzer was used to select precursor ions for fragmentation in the hexapole collision cell. The collision gas was argon at a pressure of $6-7 \times 10^{-5}$ mbar and the collision energy was 25-40 V. Product ions were analyzed using an orthogonal TOF analyzer fitted with a reflector, which is a microchannel plate detector and a time-to-digital converter. The data were processed using a peptide sequence system.

4-4: Database Searching

The MS/MS ion search was assigned as the ion search option in the MASCOT software (Matrix Science). Peptide fragment files were obtained from the peptide peaks in the ESI-MS/MS results. Trypsin was selected as the enzyme with one potentially missed cleavage site, and ESI-QTOF was selected as the instrument type. The peptide fragment files were searched based on the database using the MASCOT search engine, and the search was limited to Sus scrofa taxonomyin. Oxidized methionine was set as a variable modification, and carbamidomethylated cysteine was set as a fixed modification. The mass tolerance was set at ±1.0 and ±0.6 Da for the peptides and fragments, respectively. High scoring peptides corresponded to those that were above the default significance threshold in MASCOT (P<0.05, peptide score >35).

Figure 2B:
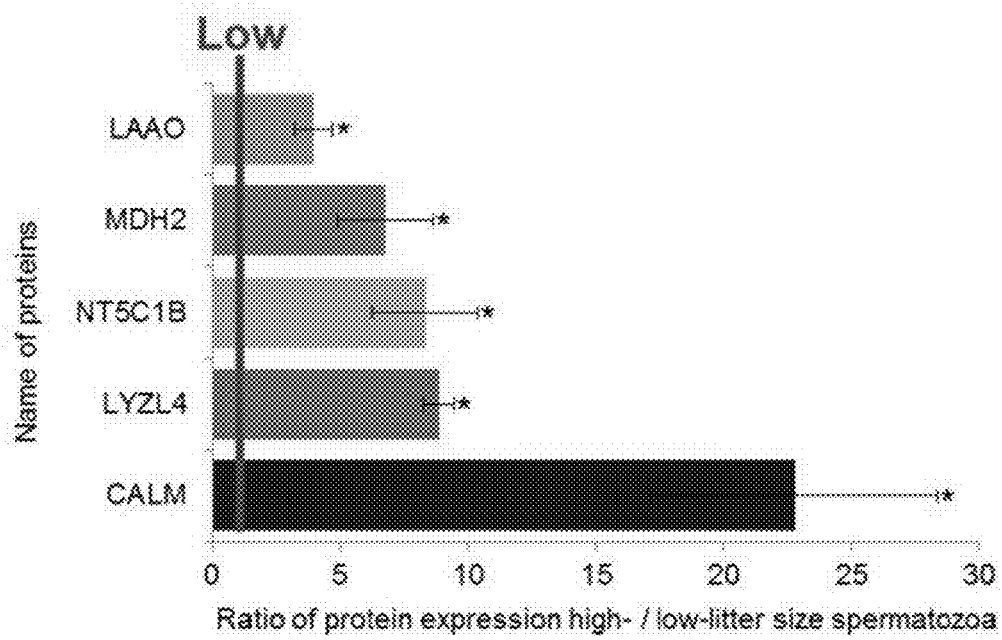

To identify fertility-related proteins, proteins from boars having high litter size and low litter size were identified by 2-DE, stained using silver staining, and then analyzed using an image analyzer. As a result, as shown in FIGS. 1 and 2, 11 spots exhibiting significantly different expression levels between high- and low-litter size spermatozoa (>3-fold; P<0.05) were screened and detected. The identified spot proteins were identified by performing an MS/MS ion search using MASCOT software. As a result, as shown in Table 2 below, the identified spots were L-amino-acid oxidase (LAAO), mitochondrial malate dehydrogenase 2, NAD (MDH2), cytosolic 5'-nucleotidase 1B (NT5C1B), lysozyme-like protein 4 (LYZL4), CALM (calmodulin), EQTN (equatorin), spermadhesin (AWN), TPI (triosephosphate isomerase), RAB2A (Ras-related protein Rab-2A), spermadhesin AQN-3 and NDUFS2 (NADH dehydrogenase [ubiquinone] iron-sulfur protein 2). Particularly, it could be seen that EQTN, AWN, TPI, RAB2A, AQN-3, and NDUFS2 were significantly highly expressed in low-litter size spermatozoa as compared to high-litter size spermatozoa (>3-fold; P<0.05; FIG. 2A), and LAAO, MDH2, NT5C1B, LYZL4, and CALM were significantly highly expressed in high-litter size spermatozoa as compared to low-litter size spermatozoa (>3-fold; P<0.05; FIG. 2B).

Table 2 below shows the results of identifying the differentially expressed proteins (>3-fold) by ESI-MS/MS.

Example I-6: Western Blotting

To confirm the 2-DE results, western blotting bands visualized using anti-RAB2A, anti-TPI, anti-NDUFS2, anti-CALM, and anti-MDH2 antibodies were quantified for three individual high- and low-litter size spermatozoa. Western blotting was performed according to a previously described method (Kwon W S et al., Fertil Steril, 99:354-61, 2013; Kwon W S et al., PLoS One, 8:e54192, 2013) with modification. The sperm samples were washed twice with DPBS (Dulbecco's phosphate-buffered saline) and centrifuged at 10,000×g for 5 min. After this, the pellets were resuspended and incubated with sample buffer containing 5% 2-mercaptoethanol for 10 min at room temperature. Then, the insoluble fractions were separated by centrifugation at 10,000×g for 10 min. The treated samples were subjected to SDS-polyacrylamide gel electrophoresis using a 12% mini-gel system (Amersham), and the separated proteins were transferred to polyvinylidene fluoride (PVDF) membranes (Amersham). The membranes were blocked with 3% blocking agent (Amersham) for 1 hour at room temperature. RAB2A, TPI, NDUFS2, CALM, and MDH2 from high- and low-litter size spermatozoa were immunodetected using anti-RAB2A and anti-CALM mouse monoclonal antibodies, anti-TPI and anti-MDH2 rabbit polyclonal antibodies, and anti-NDUFS2 goat polyclonal antibody (Amersham) that had been diluted with blocking solution (1:1,000) for 2 hours at room temperature. The membranes were then incubated with horse radish peroxidase (HRP) conjugated anti-mouse, anti-rabbit, and anti-goat IgG (Abcam) that had been diluted with blocking solution (1:3,000) for 2 hours at room tem-

TABLE 2

| gi no. | Symbol | Protein description | Peptide sequence | Mascot Score* |
|---|---|---|---|---|
| gi\|2654179 | CALM | Calmodulin | G.NGYISAAELR.H | 61 |
| gi\|31124567 | EQTN | Equatorin | R.ATTDLNFSLR.N | 60 |
| gi\|33528584 | NT5C1B | Cytosolic 5'-nucleotidase 1B | R.LINSVNHYGLLIDR.F<br>R.VAFDGDACLFSDESDHVIK.E | 59 |
| gi\|31125379 | RAB2A | Ras-related protein Rab-2A | K.LQIWDTAGQESFR.S<br>K.LLNIQPPPR.A<br>R.LVMELSGEMVR.K | 55 |
| gi\|54582230 | NDUFS2 | NADH dehydrogenase [ubiquinone] iron-sulfur protein 2 | R.IDELEEMLTNNR.I<br>K.GEFGVYLVSDGSSRPYR.C<br>K.LYTEGYQVPPGAIYIAIEAPK.G | 139 |
| gi\|80971510 | TPI | Triosephosphate isomerase | K.DLGAIWVLGHSER.R<br>K.VVLAYEPVWAIGIGK.I | 88 |
| gi\|248304 | A WN | Spermadhesin A WN | K.ICGGISLVFR.S<br>K.EYVELLDGPPGSEIIGK.I | 90 |
| gi\|31126871 | LYZL4 | Lysozyme-like protein 4 | K.FNPTAVYDNLR.G<br>R.GDYTGYGLFQIR.N | 73 |
| gi\|114083 | AQN-3 | Spermadhesin AQN-3 | F.VYQSSHNVATVK.Y<br>R.ITFIPPLTR.R | 56 |
| gi\|54583217 | LAAO | L-amino-acid oxidase | R.LALNDVAALHGPIVYR.L<br>K.ALIADAVLLIVSGPALQR.I<br>R.IYFAGEHIAFPHGWVETAVK.S | 217 |
| gi\|164541 | MDH2 | Mitochondrial malate dehydrogenase 2, NAD | K.VDFPQDQLSTLTGR.I | 59 |

*MASCOT score is -10 log (P), where P is the probability that the observed match is a random event. Individual scores > 50 indicate identity or extensive homology (P < 0.05).

perature. α-tubulin was detected by conducting incubation with a monoclonal anti-α-tubulin mouse antibody (Abcam) that had been diluted with blocking solution (1:10,000) for 2 hours at room temperature. In addition, membranes were incubated with an HRP conjugated goat anti-mouse IgG (Abcam) that had been diluted with blocking solution (1:10, 000) for 1 hour at room temperature. The membranes were washed three times with PBST. The proteins on the membranes were detected with an enhanced chemiluminescence (ECL) technique using ECL reagents. All of the bands were scanned with a GS-800 calibrated imaging densitometer (Bio-Rad), and were analyzed with Quantity One (Bio-Rad). Finally, the signal intensity ratios of the bands were calculated for RAB2A, TPI, NDUFS2, CALM, and MDH2/α-tubulin.

Figure 3A:
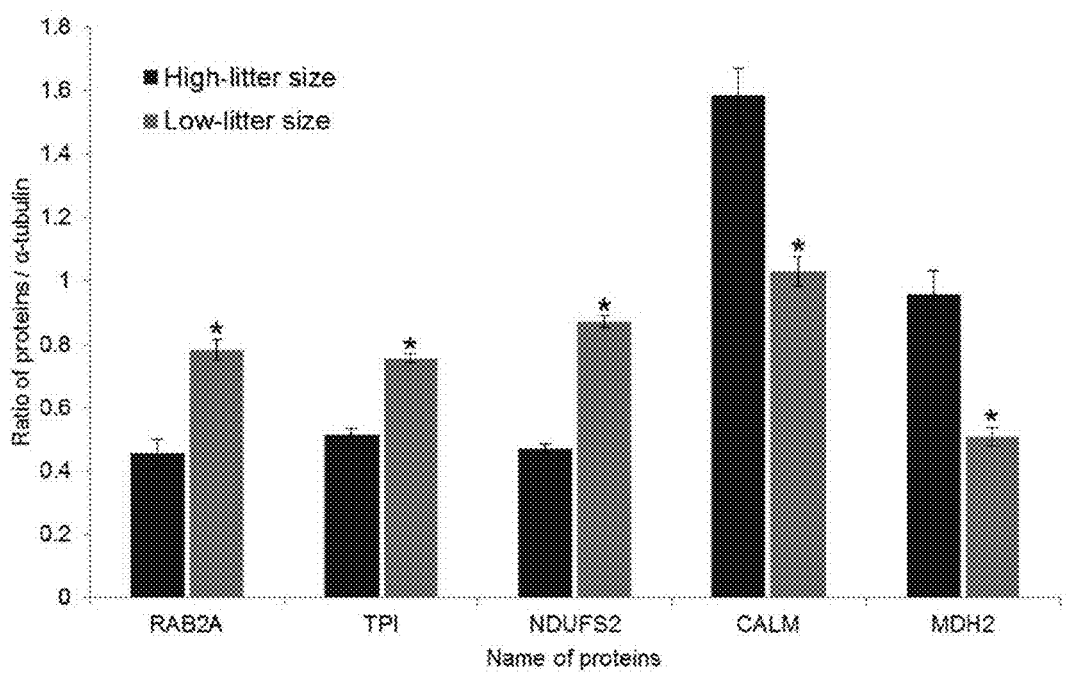
FIGS. 3A and 3B show the expression patterns of mitochondrial malate dehydrogenase 2, NAD (MDH2), CALM (calmodulin), TPI (triosephosphate isomerase), RAB2A (Ras-related protein Rab-2A) and NDUFS2 (NADH dehydrogenase [ubiquinone] iron-sulfur protein 2) in an individual having high litter size and an individual having low litter size. Specifically.
Figure 3B:
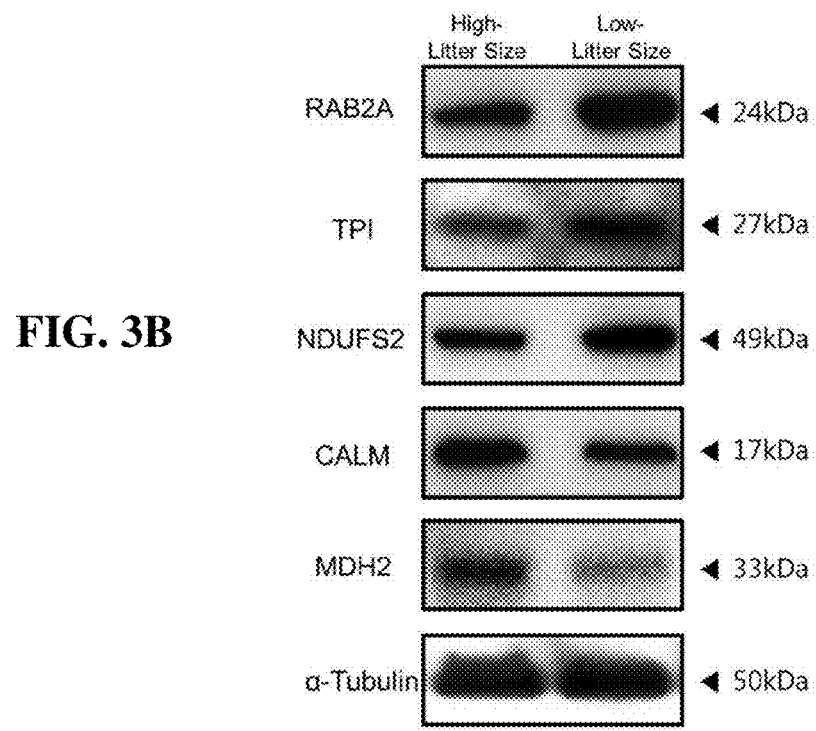

To validate the 2-DE results, the differentially expressed proteins were further examined by Western blot analysis using antibodies. As a result, RAB2A, TPI, NDUFS2, CALM, and MDH2 were detected at 24 kDa, kDa, 49 kDa, 17 kDa, and 33 kDa, respectively. These protein expression patterns were similar to the results shown in FIG. 3. Particularly, it could be seen that RAB2A, TPI, and NDUFS2 were significantly highly expressed in low-litter size spermatozoa as compared to high-litter size spermatozoa ($P<0.05$), and CALM and MDH2 were significantly highly expressed in high-litter size spermatozoa as compared to low-litter size spermatozoa ($P<0.05$).

Example I-7: ELISA (Enzyme-Linked Immunosorbent Assay)

To determine the correlation between RAB2A, TPI, NDUFS2, CALM, MDH2 and litter size in boars, an ELISA was performed with spermatozoa from 20 individual boars. Spermatozoa samples ($50 \times 10^6$/mL) for protein extractions were incubated in rehydration buffer containing 7M urea (Sigma), 2M thiourea (Sigma), 4% (w/v) CHAPS, 0.05% (v/v) Triton X-100 (Sigma), 1% (w/v) octyl β-D-glucopyranoside, 24 μM phenylmethysulfonylfluoride (PMSF), 1% (w/v) DTT, 0.05% (v/v) IPG buffer and 0.002% (w/v) bromophenol blue (BPB) at 4° C. for 1 hour.

Solubilized proteins (50 μg/well) were coated on Immuno 96-well plates, and were incubated overnight at 4° C. The plates were then blocked with blocking solution (5% [w/v] BSA in DPBS containing of 0.5% Tween-20 [PBST]) for 90 min at 37° C. After blocking, the plates were incubated with an anti-RAB2A mouse monoclonal antibody, an anti-TPI rabbit polyclonal antibody, an anti-NDUFS2 goat polyclonal antibody, an anti-CALM mouse monoclonal antibody and an anti-MDH2 rabbit polyclonal antibody, which had been diluted with blocking solution (1:5,000), for 90 min at 37° C. Then, the plates were incubated with a horseradish peroxidase (HRP) conjugated anti-mouse, anti-rabbit, and anti-goat IgG (Abcam) that had been diluted with blocking solution (1:5,000), for 90 min at 37° C. To activate the HRP, the plates were incubated with TMB solution (Sigma) for 15 min at room temperature, and the reaction was stopped with 1N sulfuric acid. Finally, the signal was measured at 450 nm using a microplate reader (Gemini Em, Molecular Devices Corporation).

To determine the correlations between litter size and the expression levels of RAB2A, TPI, NDUFS2, CALM, and MDH2, proteins were extracted from 20 boar spermatozoa, and the expression levels thereof were measured by calculating Pearson correlation coefficients. As a result, as can be seen in Table 3 below, RAB2A, TPI, and NDUFS2 were negatively correlated with litter size ($r=-0.624, -0.797$, and $-0.655$, respectively; $P<0.01$), and CALM and MDH2 were positively correlated with litter size ($r=0.665$ and $0.638$, respectively; $P<0.01$).

Table 3 below shows the correlations between litter size and the expression levels of mitochondrial malate dehydrogenase 2, NAD (MDH2), CALM (calmodulin), TPI (triose-phosphate isomerase), RAB2A (Ras-related protein Rab-2A) and NDUFS2(NADH dehydrogenase [ubiquinone] iron-sulfur protein 2) in boar spermatozoa (*$P<0.05$, **$P<0.01$).

TABLE 3

|  | Litter Size | RAB2A | TPI | NDUFS2 | CALM | MDH2 |
| --- | --- | --- | --- | --- | --- | --- |
| Litter Size | 1 | −0.624** | −0.797** | −0.655** | 0.665** | 0.638** |
| RAB2A |  |  | 0.468* | 0.615** | −0.286 | −0.360 |
| TPI |  |  |  | 0.465* | −0.422 | — |
| NDUFS2 |  |  |  |  | −0.488* | 0.587** |
| CALM |  |  |  |  |  | −0.256 |
| MDH2 |  |  |  |  |  | 0.623** |
|  |  |  |  |  |  | 1 |

MDH2 in boar spermatozoa and litter size.
*$P < 0.05$.
**$P < 0.01$.

Example I-8: Quality Assessment of Parameters

Four key parameters were used in the screening tests: sensitivity, specificity, positive predictive value, and negative predictive value (Oh S A et al., Anim Reprod Sci., 121(1-2):131-138, 2010; Oh S A et al., Int J Androl, 33(4): 604-612, 2010; Park Y J et al., J, Reprod Dev, 58(4):461-466, 2012). Sensitivity is defined as the percentage of boars that will be correctly identified by the test based on litter size. Specificity is defined as the percentage of boars that will test truly negative. The positive predictive value is defined as the percentage of boars that test positive, but actually have a litter size ≥11 or <11. The negative predictive value is defined as the percentage of boars that test negative, but actually have a litter size of ≥11 or <11.

The results of performing the quality assessment of parameters are as follows. To determine the cut-off value for litter size, an ROC curve was used. According to this curve, the cut-off expression values of RAB2A (0.118), TPI (1.115), NDUFS2 (0.930), CALM (0.275), and MDH2 (0.925) corresponded to the maximized sensitivity and specificity. Therefore, these values were established as the lower limits as shown in Table 4. The sensitivity, specificity, positive predictive value and negative predictive value of the proteins are as follows.

Figure 4A:
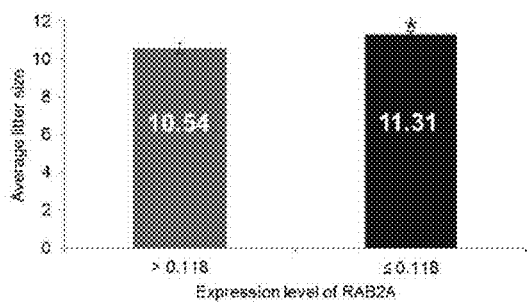
FIGS. 4A-4E show average litter size using the expression levels of mitochondrial malate dehydrogenase 2, NAD (MDH2), CALM (calmodulin), TPI (triosephosphate isomerase), RAB2A (Ras-related protein Rab-2A) and NDUFS2 (NADH dehydrogenase [ubiquinone] iron-sulfur protein 2).
Figure 4B:
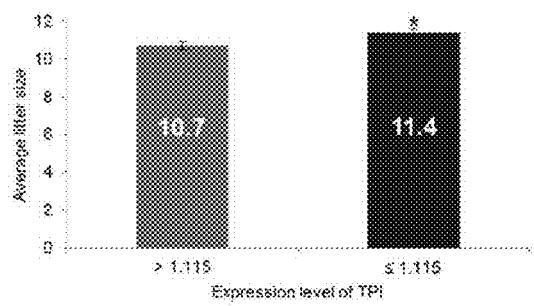

(1) In terms of the expression level of RAB2A protein, the sensitivity, specificity, negative predictive value, and positive predictive value were 90.91%, 44.44%, 80.00%, and 66.67%, respectively. The overall accuracy of the prediction of eleven litters was 70.00% (Table 4). As shown in FIG. 4A, the low litter size of boars above the cut-off (>0.118) was 10.54 piglets, whereas the average litter size of boars below the cut-off (≤0.118) was 11.31 piglets.

(2) The sensitivity, specificity, negative predictive value, and positive predictive value of TPI protein were 72.73%, 44.44%, 57.14%, and 61.54%, respectively. The overall accuracy of the prediction of litter size ≥11 was 60.00% (Table 4). As shown in FIG. 4A, the average litter size of boars above the cut-off (>1.115) was 10.70 piglets, and the average litter size of boars below the cut-off (≤1.115) was 11.4 piglets (P<0.05).

Figure 4C:
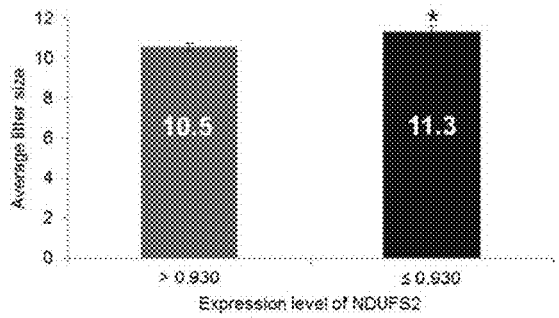

(3) Regarding NDUFS2 protein, the sensitivity, specificity, negative predictive value, and positive predictive values were 90.91%, 44.44%, 80.00%, and 66.67%, respectively. The overall accuracy of the prediction of litter size ≥11 was 70.00% (Table 4). As shown in FIG. 4C, the average litter size of boars above the cut-off (>0.930) was 10.54 piglets, whereas the average litter size of boars below the cut-off (≤0.930) was 11.31 piglets (P<0.05).

Figure 4D:
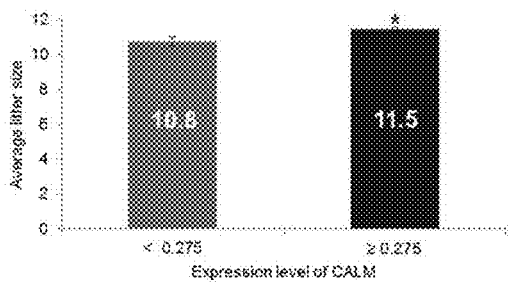

(4) The sensitivity, specificity, negative predictive value, and positive predictive value of CALM protein were 81.82%, 88.89%, 80.00%, and 90.00%, respectively. The overall accuracy of the prediction of litter size ≥11 was 85.00% (Table 4). As shown in FIG. 4D, the average litter size of boars below the cut-off (<0.275) was 10.77 piglets, and the average litter size of boars above the cut-off (≥0.275) was 11.46 piglets (P<0.05).

Figure 4E:
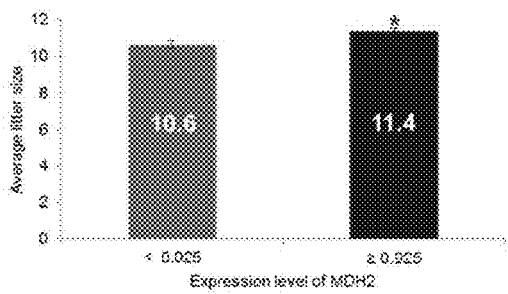

(5) Regarding MDH2 protein, the sensitivity, specificity, negative predictive value, and positive predictive values were 90.91%, 66.67%, 85.71%, and 76.92%, respectively. The overall accuracy of the prediction of litter size ≥11 was 80.00% (Table 4). As shown in FIG. 4E, the average litter size of boars below the cut-off (<0.925) was 10.64 piglets, whereas the average litter size of boars above the cut-off (≥0.925) was 11.37 piglets (P<0.05).

Table 4 below shows the correlations between litter size and the expression levels of mitochondrial malate dehydrogenase 2, NAD (MDH2), CALM (calmodulin), TPI (triosephosphate isomerase), RAB2A (Ras-related protein Rab-2A) and NDUFS2 (NADH dehydrogenase [ubiquinone] iron-sulfur protein 2).

TABLE 4

|  | Sensitivity (%) | Specificity (%) | Negative predictive value (%) | Positive predictive value (%) | Overall accuracy (%) |
|---|---|---|---|---|---|
| RAB2A | 90.9 | 44.4 | 80 | 66.7 | 70 |
| TPI | 72.7 | 44.4 | 57.1 | 61.5 | 60 |
| NDUFS2 | 90.9 | 44.4 | 80 | 66.7 | 70 |
| CALM | 81.8 | 88.9 | 80 | 90 | 85 |
| MDH2 | 90.9 | 66.7 | 85.7 | 76.9 | 80 |

Example I-9: Signaling Pathway

Figure 5:
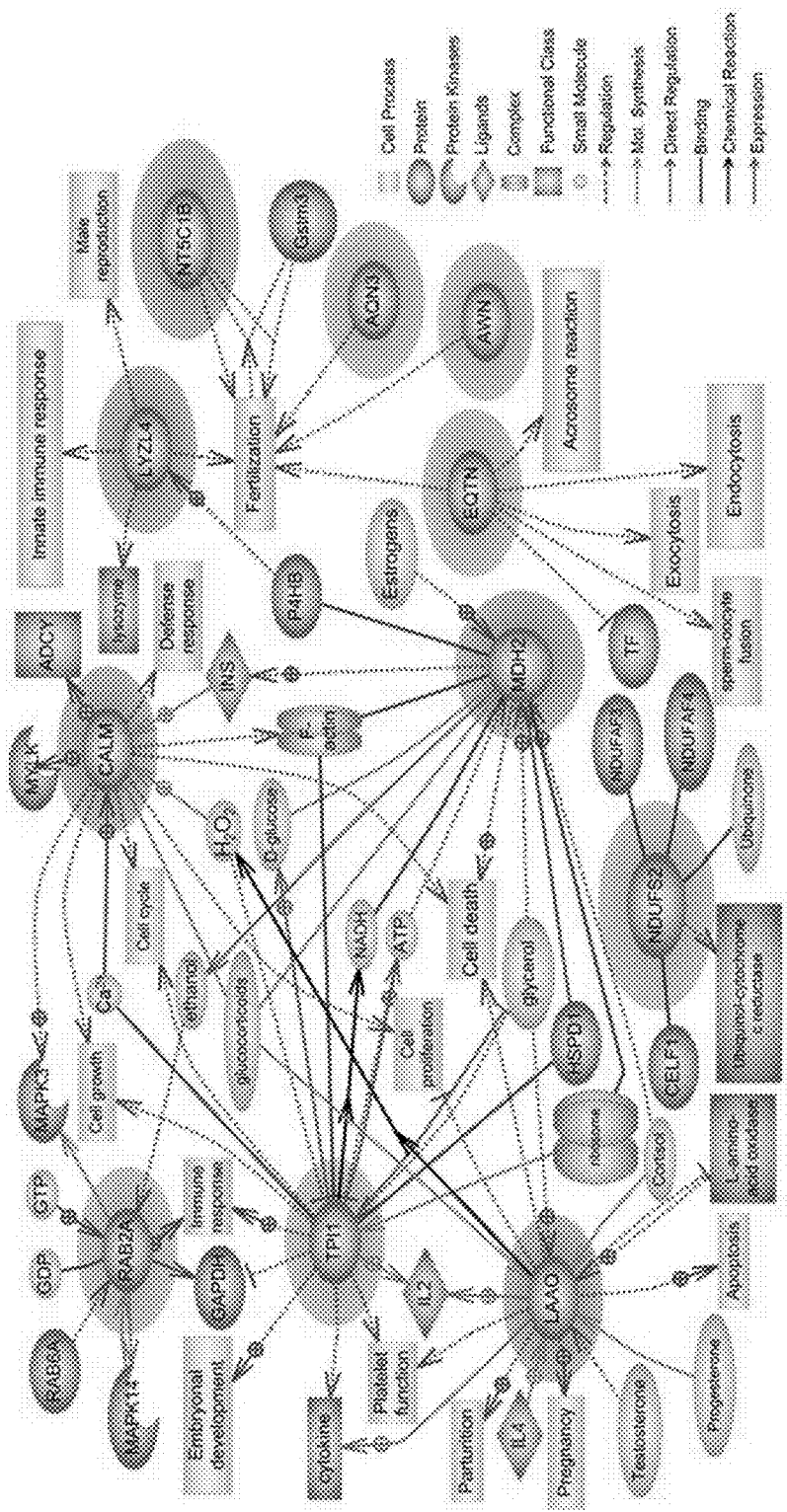
FIG. 5 shows signaling pathways associated with litter size in boars. Red highlighted proteins were abundantly expressed in high-litter size spermatozoa, and blue highlighted proteins were abundantly expressed in low-litter size spermatozoa.

To visualize the biological functions and signaling pathways between the differentially expressed proteins, the Pathway Studio program (v 9.0, Aridane Genomics) was used. Analysis was performed by Pathway Studio. As a result, as shown in FIG. 5, the identified sperm marker proteins, L-amino-acid oxidase (LAAO), mitochondrial malate dehydrogenase 2, NAD (MDH2), cytosolic 5'-nucleotidase 1B (NT5C1B), lysozyme-like protein 4 (LYZL4), CALM (calmodulin), EQTN (equatorin), spermadhesin AWN, TPI (triosephosphate isomerase), RAB2A (Ras-related protein Rab-2A), spermadhesin AQN-3 and NDUFS2 (NADH dehydrogenase [ubiquinone] iron-sulfur protein 2), interacted with each other, and were also related to particular cell processes, protein kinases, ligands, complexes, functional classes, and small molecules.

Example I-10: Statistical Analysis

Statistical analysis was performed using software program SPSS version 18.0 (USA). Pearson correlation coefficients were calculated to determine the correlations between litter size and the expression levels of RAB2A, TPI, NDUFS2, CALM, and MDH2.

Receiver-operating curves (ROCs) were used to assess the utility of individual analyzed parameters as a means of identifying litter size ≥11 or <11 (based on average litter size). The cut-off value was calculated by ROCs, and it was determined in relation to the point of maximized specificity and sensitivity (Oh S A et al., Anim Reprod Sci., 121(1-2): 131-138, 2010; Oh S A et al., Int J Androl, 33(4):604-612, 2010; Park Y J et al., J, Reprod Dev, 58(4):461-466, 2012).

Student's two-tailed t-test was used to compare protein expression levels and predicted litter size by ROCs. P<0.05 was considered significantly different. All data are expressed as mean±SEM.

II. Method of Predicting Animal Semen Quality and Litter Size Using Chlortetracycline Staining Example II-1: Semen Source and Artificial Insemination Landrace semen samples were randomly collected from grand-grandparents farm of Sunjin Co. (Danyang, Korea). Parity data (total pups/total breeding) were obtained from the farm. Based on the data, 17 samples were collected from 27 boars having an average litter size of 11.47±1.19. Each of the collected semen samples were diluted in 100 m of extender (Beltsville thawing solution) to a density of 30×10 sperm cells/mL, and then stored at 17° C.

The stored semen within 3 days after ejaculation was first inseminated within 24 hours after estrus of sows, and 24 hours after the first insemination, second artificial insemination was performed. Data related to the fertility of the boars that have been inseminated as described above were collected.

For semen analysis, the extended semen collected within 2 hours was used. The semen was washed with DPBS (Dulbecco's phosphate-buffered saline) at 1,500×g for 10 minutes, and then divided into two parts so that it could be used before and after capacitation. For a capacitation experiment, the semen parts were incubated with mTCM (modified tissue culture media) 199 medium containing FBS (fetal bovine serum (v/v), 0.91 mM sodium pyruvate, 3.05 mM D-glucose, 2.92 mM calcium lactate and 10 μg/mL heparin in the presence of 5% $CO_2$ in air at 37° C. (Oh S A et al., Animal Reproduction Science, 121:131-138, 2010).

All procedures were performed according to guidelines for the ethical treatment of animals, and were approved by the Institutional Animal Care and Use Committee of Chung-Ang University.

Example II-2: CASA (Computer-Assisted Sperm Analysis)

Sperm motility (%) and motion kinematics were analyzed by computer-assisted sperm analysis using a CASA system (SAIS Plus version 10.1, Medical Supply, Seoul, Korea). Specifically, 10 μL of the sperm of each group prepared in Example 1 was placed in a Makler chamber (Makler, Israel) on a heated stage. Using a 10× objective in phase contrast mode, the image was relayed, digitized, and analyzed by SAIS. The movement of at least 250 sperm cells was recorded for each sample from random fields. Program settings were as follows: frame acquired: 20; frame rate: 30 Hz; minimum contrast: 7; minimum size: 5; low/high size gates: 0.4-1.5; low/high intensity gate: 0.4-1.5; nonmotile head size: 16; nonmotile brightness: 14. With respect to the motility setting parameters, objects with a curvilinear velocity (VCL) more than 10 μm/s were considered motile. Motility (%) and five motion kinematics parameters (i.e., curvilinear velocity (VCL, μm/s), straight-line velocity (VSL, μm/s), average path velocity (VAP, μm/s), and mean amplitude of head lateral displacement (ALH, μm) were analyzed.

The correlations between litter size and sperm motility and motion kinematics before and after capacitation and according to the difference between before and after capacitation were examined. As a result, as shown in Table 5 below, sperm mobility and motion kinematics did not show a significant correlation with litter size before and after capacitation and according to the difference between before and after capacitation. Table 5 below shows correlations between litter size and sperm motility and motion kinematics, before and after capacitation, and according to the difference (Δ) between before and after capacitation.

TABLE 5

| | Litter Size | | | | | | | | | |
|---|---|---|---|---|---|---|---|---|---|---|
| | Before-capacitation (BC) | | | | | | After-capacitation (AC) | | | |
| | MOT | VCL | VSL | VAP | LIN | ALH | MOT | VCL | VSL | VAP |
| Litter Size | −0.129 | −0.182 | −0.321 | −0.314 | −0.071 | −0.222 | 0.030 | 0.049 | −0.243 | −0.174 |
| MOT (BC) | | −0.037 | 0.532** | 0.297 | 0.280 | 0.219 | 0.811* | 0.282 | −0.130 | 0.088 |
| VCL (BC) | | | 0.355* | 0.519** | −0.548** | 0.634** | −0.023 | 0.569 | −0.215 | −0.197 |
| VSL (BC) | | | | 0.855** | −0.016 | 0.790** | 0.424* | 0.307 | −0.034 | 0.077 |
| VAP (BC) | | | | | −0.310 | 0.899** | 0.203 | 0.317 | −0.025 | 0.059 |
| LIN (BC) | | | | | | −0.590** | 0.149 | −0.142 | 0.343* | 0.282 |
| ALH (BC) | | | | | | | 0.223 | 0.327* | −0.193 | −0.068 |
| MOT (AC) | | | | | | | | 0.612** | 0.056 | 0.296 |
| VCL (AC) | | | | | | | | | 0.281 | 0.573** |
| VSL (AC) | | | | | | | | | | 0.940** |
| VAP (AC) | | | | | | | | | | |
| LIN (AC) | | | | | | | | | | |
| ALH (AC) | | | | | | | | | | |
| MOT (Δ) | | | | | | | | | | |
| VCL (Δ) | | | | | | | | | | |
| VSL (Δ) | | | | | | | | | | |
| VAP (Δ) | | | | | | | | | | |
| LIN (Δ) | | | | | | | | | | |

| | Litter Size | | | | | | | |
|---|---|---|---|---|---|---|---|---|
| | After-capacitation (AC) | | Differences (Δ) before and after capacitation | | | | | |
| | LIN | ALH | MOT | VCL | VSL | VAP | LIN | ALH |
| Litter Size | −0.274 | −0.036 | 0.177 | 0.187 | −0.067 | 0.081 | −0.272 | 0.167 |
| MOT (BC) | −0.296 | 0.203 | −0.396* | 0.178 | −0.354* | −0.161 | −0.495** | −0.051 |
| VCL (BC) | −0.259 | −0.089 | 0.014 | −0.858** | −0.349* | −0.514** | −0.022 | −0.592** |
| VSL (BC) | −0.245 | 0.237 | −0.097 | −0.159 | −0.482** | −0.544* | −0.278 | −0.519** |
| VAP (BC) | −0.263 | 0.246 | −0.027 | −0.301 | −0.409** | −0.660* | −0.126 | −0.606** |
| LIN (BC) | 0.480** | 0.062 | −0.139 | 0.417* | 0.308 | 0.416* | −0.014 | 0.550** |
| ALH (BC) | −0.449** | 0.170 | 0.015 | −0.390* | −0.527** | −0.684** | −0.181 | −0.745** |
| MOT (AC) | −0.327* | 0.536** | 0.483** | 0.335* | −0.143 | 0.080 | −0.455** | 0.171 |
| VCL (AC) | −0.375* | 0.916* | 0.397* | 0.453* | 0.108 | 0.208 | −0.348* | 0.339** |
| VSL (AC) | 0.776** | 0.624** | 0.298 | 0.337* | 0.892** | 0.725** | 0.692** | 0.589** |
| VAP (AC) | 0.528** | 0.840** | 0.334* | 0.471** | 0.789** | 0.711** | 0.454** | 0.627** |
| LIN (AC) | | 0.008 | −0.051 | 0.065 | 0.791** | 0.582** | 0.870** | 0.392* |
| ALH (AC) | | | 0.396* | 0.533** | 0.440* | 0.459** | −0.025 | 0.531** |
| MOT (Δ) | | | | 0.192 | 0.225 | 0.271 | 0.020 | 0.255 |
| VCL (Δ) | | | | | 0.365* | 0.565** | −0.160 | 0.784** |
| VSL (Δ) | | | | | | 0.852** | 0.729** | 0.751** |
| VAP (Δ) | | | | | | | 0.430** | 0.899** |
| LIN (Δ) | | | | | | | | 0.138 |

MOT = motility (%); VCL = curvilinear velocity (μm/s); VSL = straight-line velocity (μm/s); VAP = average path velocity (μm/s); LIN = linearity; ALH = mean amplitude of head lateral displacement (μm).
*$P < 0.05$.
**$P < 0.01$.

Example II-3: Hoechst 33258/Chlortetracycline Fluorescence Assessment of Capacitation Status To determine capacitation status, a conventional dual staining method was used with a slight modification (Kwon W S et al., Fertil Steril, 99:354-61, 2013; Kwon W S et al., PLoS One, e54192, 2013). Briefly, 135 μL of non-capacitated spermatozoa or capacitated spermatozoa were added to 15 μL of H33258 solution (DPBS (Dulbecco's Phosphate-Buffered Saline) containing 10 μM H33258) and incubated for 10 min at room temperature. Excess dye was removed by layering the mixture over 250 μL of 2% (w/v) polyvinylpyrrolidone in DPBS. After centrifuging at 400×g for 10 min, the supernatant was discarded, and the pellet was resuspended in 500 μL of DPBS and a chlortetracycline fluorescence solution (750 mM CTC in 5 μl buffer: 20 mM Tris, 130 mM NaCl, and 5 mM cysteine, pH 7.4). Samples were observed with a Nikon microphot-FXA microscope (Tokyo, Japan) under epifluorescence illumination using ultraviolet BP 340-380/LP 425 and BP 450-490/LP 515 excitation/emission filters for H33258 and CTC, respectively. The spermatozoa were classified as live non-capacitated (F pattern, bright green fluorescence distributed uniformly over the entire sperm head, with or without a stronger fluorescent line at the equatorial segment), live capacitated (B pattern, green fluorescence over the acrosomal region and a dark postacrosome), or live acrosome reacted (AR, sperm showing a mottled green fluorescence over the head, green fluorescence only in the postacrosomal region, or no fluorescence over the head) (Kwon W S et al., Fertil Steril, 99:354-61, 2013; Kwon W S et al., PLoS One, e54192, 2013). Two slides per sample were evaluated with at least 400 spermatozoa per slide.

The correlations between litter size and sperm capacitation status before and after capacitation and between litter size and the difference between before and after capacitation were examined. As a result, as shown in Table 6 below, AR after capacitation was positively correlated with litter size ($r=0.375$; $P<0.05$). Also, the difference (Δ) in AR and B patterns between before and after capacitation showed a significant correlation with litter size. As shown in Table 6 below, the difference (Δ) in AR pattern between before and after capacitation showed a positive correlation with litter size ($r=0.333$; $P<0.05$), and the difference (Δ) in B pattern between before and after capacitation showed a negative correlation with litter size ($r=-196$ 0.477; $P<0.05$). Table below shows the correlations between litter size and boar sperm capacitation before and after capacitation and between litter size and the difference (Δ) between before and after capacitation.

is defined as the percentage of boars that will test truly negative. The positive predictive value is defined as the percentage of boars that test positive, but actually have a litter size ≥12 or <12. The negative predictive value is defined as the percentage of boars that test negative, but actually have a litter size of ≥12 or <12.

To confirm capacitation status, spermatozoa were stained with Hoechst 33258/chlortetracycline according to the method of Example II-3, and classified according to whether they were capacitated. Then, the quality of parameters in capacitation status was assessed in the same manner as described in Example II-4. To determine the cut-off value for a litter size of 12, the AR pattern after capacitation (17.5%), the difference in AR pattern between before and after capacitation (Δ=18.97%), and the AR pattern after capacitation (17.5%), the difference in B pattern between before and after capacitation (Δ=0.68%) were established as lower limits (Tables 7, 8 and 9). Table 7 below shows the correlation between litter size and the percentage of AR pattern after boar sperm capacitation; Table 8 below shows the correlation between litter size and the percentage of the difference (Δ) in AR pattern between before and after capacitation of boar sperm capacitation; and Table 9 below shows the correlation between litter size and the percentage of the difference (Δ) in B pattern between before and after capacitation of boar sperm capacitation.

TABLE 7

| | Litter size ≥ 12 | Litter size < 12 |
|---|---|---|
| AR (AC) ≥ 17.5% (n = 12) | 6[A] | 6[B] |
| AR (AC) < 17.5% (n = 15) | 2[C] | 13[D] |
| Sensitivity | 75 | |
| Specificity | 68.4 | |
| Negative predictive value | 86.7 | |
| Positive predictive value | 50 | |
| Overall accuracy | 70 | |

Sensitivity = [A/(A + C)] × 100; Specificity = [D/(B + D)] × 100; Positive predictive value = [A/(A + B)] × 100; Negative predictive value = [C/(C + D)] × 100; and overall accuracy = [(A + D)/(A + B + C + D)] × 100.

TABLE 6

| | Litter Size | | | | | | | | |
|---|---|---|---|---|---|---|---|---|---|
| | Before-capacitation (BC) | | | After-capacitation (AC) | | | Differences (Δ) before and after capacitation | | |
| | AR | B | F | AR | B | F | AR | B | F |
| Litter Size | 0.298 | 0.230 | −0.311 | 0.37*' | −0.156 | −0.276 | 0.333** | −0.447** | −0.002 |
| AR (BC) | | 0.072 | −0.398* | 0.544** | −0.118 | −0.492** | 0.310 | −0.221 | −0.152 |
| B (BC) | | | −0.943** | −0.144 | 0.627** | −0.398** | −0.151 | −0.409* | 0.473** |
| F (BC) | | | | −0.076 | −0.538** | 0.529** | 0.036 | 0.449** | −0.384* |
| AR (AC) | | | | | −0.481** | −0.685** | 0.966** | −0.433* | −0.672** |
| B (AC) | | | | | | −0.310 | −0.509** | 0.454** | 0.179 |
| F (AC) | | | | | | | −0.625** | 0.093 | 0.580** |
| AR (Δ) | | | | | | | | −0.423* | −0.715** |
| B (Δ) | | | | | | | | | −0.331* |

F = non-capacitated sperm; B = capacitated sperm; AR = acrosome-reacted sperm.
*P < 0.05.
**P < 0.01.

Example II-4: Quality Assessment of Parameters

The following four key parameters were used in the screening tests: sensitivity, specificity, positive predictive value, and negative predictive value (Evans M I et al., Clinical Obstetrics and Gynecology, 45:657-660, 2002). Sensitivity is defined as the percentage of boars that will be correctly identified by the test based on litter size. Specificity

TABLE 8

| | Litter size ≥ 12 | Litter size < 12 |
|---|---|---|
| AR (Δ) ≥ 18.97% (n = 11) | 5[A] | 6[B] |
| AR (Δ) < 18.97% (n = 16) | 3[C] | 13[D] |
| Sensitivity | 62.5 | |
| Specificity | 68.4 | |

TABLE 8-continued

|  | Litter size ≥ 12 | Litter size < 12 |
|---|---|---|
| Negative predictive value |  | 81.3 |
| Positive predictive value |  | 45.5 |
| Overall accuracy |  | 70 |

Sensitivity = [A/(A + C)] × 100; Specificity = [D/(B + D)] × 100; Positive predictive value = [A/(A + B)] × 100, negative predictive value = [C/(C + D)] × 100, and overall accuracy = [(A + D)/(A + B + C + D)] × 100.

TABLE 9

|  | Litter size ≥ 12 | Litter size < 12 |
|---|---|---|
| B (Δ) ≤ 0.68% (n = 11) | 6$^A$ | 4$^B$ |
| B (Δ) > 0.68% (n = 16) | 2$^C$ | 15$^D$ |
| Sensitivity |  | 75 |
| Specificity |  | 79 |
| Negative predictive value |  | 88.2 |
| Positive predictive value |  | 60 |
| Overall accuracy |  | 70 |

Sensitivity = [A/(A + C)] × 100; Specificity = [D/(B + D)] × 100; Positive predictive value = [A/(A + B)] × 100; Negative predictive value = [C/(C + D)] × 100; and overall accuracy = [(A + D)/(A + B + C + D)] × 100.

Figure 6A:
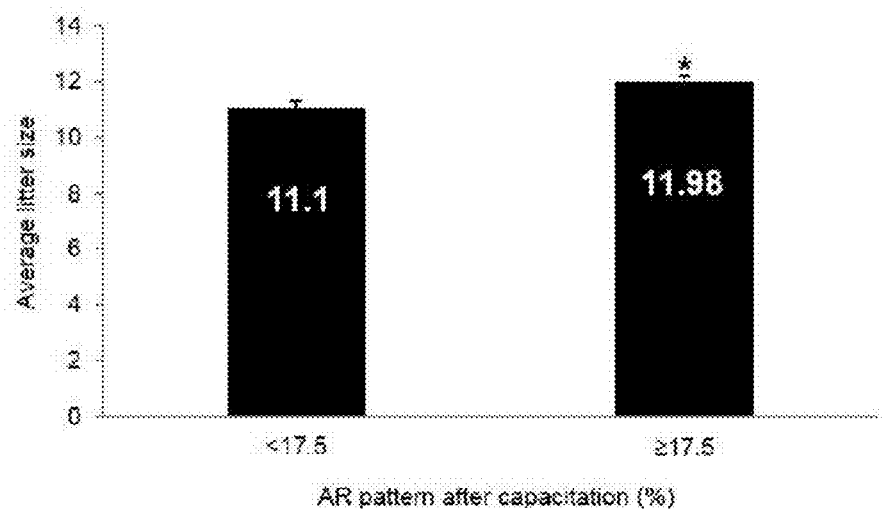
FIGS. 6A-6C show average litter size predicted using AR pattern and the differences in AR and B patterns.

Regarding the AR pattern after capacitation, 6 boars showed an AR patter of ≥17.5% and were predicted to produce ≥12 piglets, but 6 boars were predicted to produce 12 or less piglets. Meanwhile, 2 boars showed an AR pattern of 17.5% or less and were predicted to produce ≥12 piglets, and the remaining 13 boars were predicted to produce 12 or less piglets. The sensitivity, the specificity, the negative predictive value and the positive predictive value were 75, 68.4, 86.7 and 50%, respectively. As shown in Table 7 above, the overall accuracy of prediction with a litter size of 12 was 70%. As shown in FIG. 6A, when the AR pattern after boar capacitation was 17.5% or less, the average litter size was 11.1 piglets, but when the AR pattern after boar capacitation was ≥17.5%, the average litter size was 11.98 piglets (P<0.05).

Figure 6B:
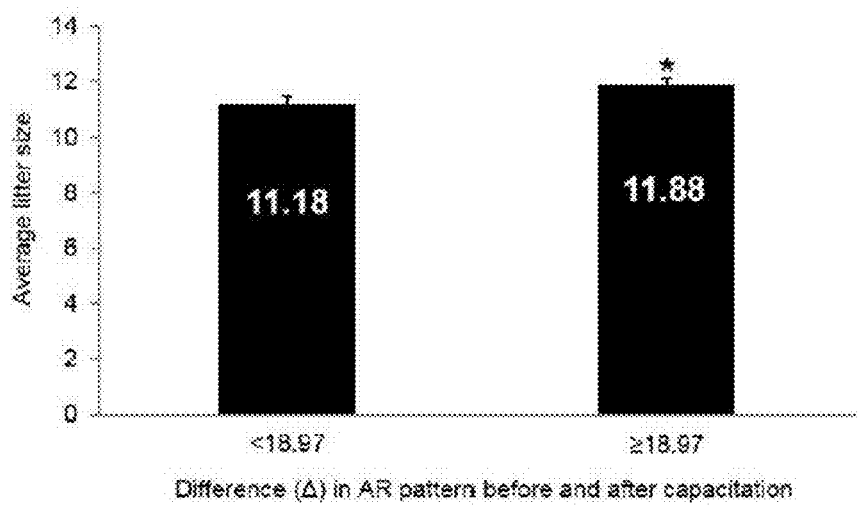

5 boars having a difference (Δ) in AR pattern of ≥18.97% between before and after capacitation were predicted to produce ≥12 piglets, whereas the remaining 6 boars were predicted to produce 12 or less piglets. 3 boars having a difference (Δ) in AR pattern of 18.97% or less between before and after capacitation were predicted to produce ≥12 piglets (13 boars were predicted to produce 12 or less piglets). The sensitivity, the specificity, the negative predictive value and the positive predictive value were 62.5, 68.4, 81.3 and 45.5%, respectively. As shown in Table 8 above, the overall accuracy of prediction with a litter size of ≥12 was 70%. As shown in FIG. 6B, when the difference (Δ) in AR pattern between before and after capacitation was 18.97% or less, the average litter size was 11.18 piglets, but when the difference (Δ) in AR pattern between before and after capacitation was ≥18.97%, the average litter size was 11.88 piglets (P<0.05).

Figure 6C:
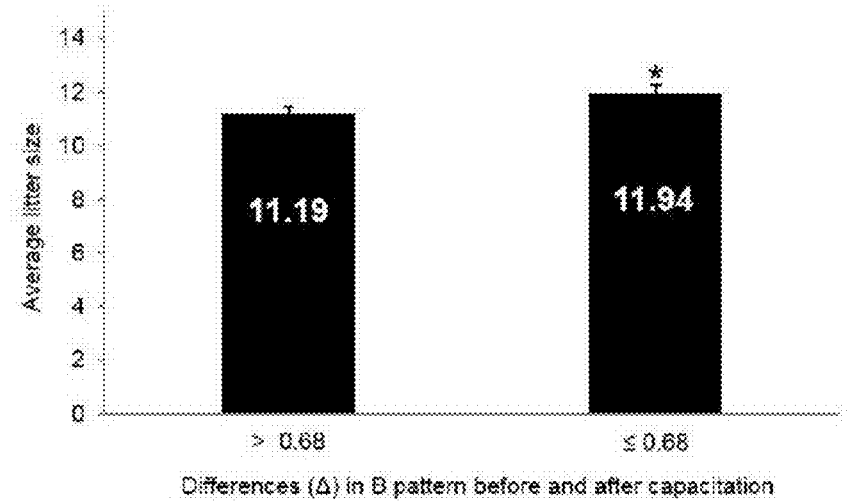

6 boars having a difference (Δ) in B pattern of ≤0.68% between before and after capacitation were predicted to produce 12 or more piglets, but 4 boars were predicted to produce 12 or less piglets. Meanwhile, 2 boars having a difference (Δ) in B pattern of 0.68% or more between before and after capacitation were predicted to produce ≥12 piglets, and 15 boars were predicted to produce 12 or less piglets. The sensitivity, the specificity, the negative predictive value and the positive predictive value were 75, 79, 88.2 and 60%, respectively. As shown in Table 9 above, the overall accuracy of prediction with a litter size of ≥12 was 70%. As shown in FIG. 6C, when the difference (Δ) in B pattern between before and after capacitation was 0.68% or more, the average litter size was 11.19 piglets, but when the difference (Δ) in B pattern between before and after capacitation was ≤0.68%, the average litter size was 11.94 piglets (P<0.05).

Example II-5: Statistical Analysis

Statistical analysis was performed using software program SPSS version 18.0 (USA). Pearson correlation coefficients were calculated to determine the correlation between litter size and the motility, motion kinematics and capacitation status of spermatozoa according to capacitated sperm/non-capacitated sperm or a change in capacitation status.

Receiver-operating curves (ROCs) were used to assess the utility of individual analyzed parameters as a means of identifying litter size ≥12 or <12 (based on average litter size). The cut-off value was calculated by ROCs, and it was determined in relation to the point of maximized specificity and sensitivity (Oh S A et al., Anim Reprod Sci., 121(1-2): 131-138, 2010; Oh S A et al., Int J Androl, 33(4):604-612, 2010; Park Y J et al., J, Reprod Dev, 58(4):461-466, 2012). Student's two-tailed t-test was used to compare predicted litter by ROCs. P<0.05 was considered significantly different. All data are expressed as mean±SEM.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of selecting a porcine male animal for breeding on a predictive basis, and breeding said animal, for a predetermined litter size criterion, said method comprising:

selecting the predetermined litter size criterion;
obtaining a sample of sperm from a candidate porcine male animal;
contacting the sample with an anti-calmodulin antibody to induce a calmodulin-antibody reaction;
detecting a level of calmodulin in a calmodulin-antibody reaction product of the calmodulin-antibody reaction by an ELISA assay, wherein the ELISA assay is carried out using an anti-calmodulin mouse antibody, and wherein the anti-calmodulin mouse antibody is a monoclonal antibody or a polyclonal antibody;
conducting a computer-implemented assessment of said calmodulin level in a receiver operating characteristic (ROC) analysis establishing a cut-off value based on (i) sensitivity as a percentage of like animals that will be correctly identified based on the predetermined litter size criterion, (ii) specificity as a percentage of like animals that will test truly negative based on the predetermined litter size criterion, (iii) positive predictive value as a percentage of like animals that test positive but actually have a litter size that is at least equal to the predetermined litter size criterion or that actually have a litter size that is less than the predetermined litter size criterion, and (iv) negative predictive value as a percentage of like animals that test negative, but that actually have a litter size at least equal to the predetermined litter size criterion or actually have a litter size less than the predetermined litter size criterion, to identify whether said animal satisfies the predetermined litter size criterion based on the relationship of said calmodulin level to said cut-off value, wherein said cut-off value is 0.275; and breeding said animal if said animal predictively satisfies the predetermined litter size criterion, with a cut-off value equal to or above said cut-off value of 0.275.

2. The method of claim 1, wherein the method is carried out with a plurality of candidate porcine male animals.

3. The method of claim 1, wherein the ELISA assay is carried out using a label-conjugated secondary antibody and a chromogenic substrate solution.

4. The method of claim 1, wherein the anti-calmodulin mouse antibody is an immunologically-active antibody fragment, a humanized version of the anti-calmodulin mouse antibody, a genetically engineered single-chain Fv molecule, or a chimeric version of the anti-calmodulin mouse antibody.

5. The method of claim 1, wherein said predetermined litter size criterion is selected as a litter size of at least 11.

* * * * *

UNITED STATES PATENT AND TRADEMARK OFFICE
CERTIFICATE OF CORRECTION

PATENT NO. : 10,288,624 B2
APPLICATION NO. : 14/711741
DATED : May 14, 2019
INVENTOR(S) : Pang et al.

Page 1 of 2

It is certified that error appears in the above-identified patent and that said Letters Patent is hereby corrected as shown below:

In the Specification

In Table 5 at Columns 21-22, upper table portion:
In row "MOT (BC)", under "Before-capacitation (BC)", under column "VAP", "0.297" should be -- 0.237 --.
In row "MOT (BC)", under "After-capacitation (AC)", under column "MOT", "0.811" should be -- 0.611 --.
In row "MOT (BC)", under "After-capacitation (AC)", under column "VAP", "0.088" should be -- 0.008 --.
In row "VCL (BC)", under "After-capacitation (AC)", under column "VCL", "0.569" should be -- 0.069 --.
In row "LIN (BC)", under "After-capacitation (AC)", under column "MOT", "0.149" should be -- 0.148 --.
In row "LIN (BC)", under "After-capacitation (AC)", under column "VAP", "0.282" should be -- 0.262 --.

In Table 5 at Columns 21-22, lower table portion:
In row "Litter Size", under "Differences (Δ) before and after capacitation", under column "VAP", "0.081" should be -- 0.091 --.
In row "MOT (BC)", under "Differences (Δ) before and after capacitation", under column "MOT", "-0.396" should be -- - 0.398 --.
In row "VCL (BC)", under "After-capacitation (AC)", under column "LIN", "-0.259" should be -- - 0.289 --.
In row "VCL (BC)", under "After-capacitation (AC)", under column "ALH", "-0.089" should be -- - 0.069 --.
In row "VSL (BC)", under "Differences (Δ) before and after capacitation", under column "LIN", "-0.278" should be -- - 0.270 --.
In row "ALH (BC)", under "Differences (Δ) before and after capacitation", under column "VCL", "-0.390" should be -- - 0.399 --.

Signed and Sealed this
Ninth Day of July, 2019

Andrei Iancu
*Director of the United States Patent and Trademark Office*

CERTIFICATE OF CORRECTION (continued)
U.S. Pat. No. 10,288,624 B2

In row "VSL (AC)", under "Differences (Δ) before and after capacitation", under column "MOT", "0.298" should be -- 0.208 --.
In row "MOT (Δ)", under "Differences (Δ) before and after capacitation", under column "VSL", "0.225" should be -- 0.226 --.
In row "VCL (Δ)", under "Differences (Δ) before and after capacitation", under column "VSL", "0.365" should be -- 0.368 --.
In row "VCL (Δ)", under "Differences (Δ) before and after capacitation", under column "VAP", "0.565" should be -- 0.566 --.
In row "VCL (Δ)", under "Differences (Δ) before and after capacitation", under column "ALH", "0.784" should be -- 0.704 --.
In row "VSL (Δ)", under "Differences (Δ) before and after capacitation", under column "VAP", "0.852" should be -- 0.882 --.

In Table 6 at Columns 23-24:
In row "Litter Size", under "After-capacitation (AC)", under column "AR", "0.37" should be -- 0.375 --.